(12) United States Patent
Kern et al.

(10) Patent No.: US 9,309,511 B2
(45) Date of Patent: Apr. 12, 2016

(54) FUNCTIONAL ASSAY FOR IDENTIFICATION OF LOSS-OF-FUNCTION MUTATIONS IN GENES

(75) Inventors: Scott E. Kern, Hunt Valley, MD (US); Eike Gallmeier, Germering (DE); Tomas Hucl, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 398 days.

(21) Appl. No.: 12/675,968

(22) PCT Filed: Aug. 28, 2008

(86) PCT No.: PCT/US2008/010233
§ 371 (c)(1),
(2), (4) Date: Aug. 9, 2010

(87) PCT Pub. No.: WO2009/032185
PCT Pub. Date: Mar. 12, 2009

(65) Prior Publication Data
US 2010/0305001 A1    Dec. 2, 2010

Related U.S. Application Data

(60) Provisional application No. 60/966,404, filed on Aug. 28, 2007, provisional application No. 61/067,610, filed on Feb. 29, 2008.

(51) Int. Cl.
*C12Q 1/68* (2006.01)
*C12N 15/10* (2006.01)
*C40B 30/06* (2006.01)

(52) U.S. Cl.
CPC ............ *C12N 15/1082* (2013.01); *C40B 30/06* (2013.01)

(58) Field of Classification Search
None
See application file for complete search history.

(56) References Cited

U.S. PATENT DOCUMENTS

| 5,527,676 A | 6/1996 | Vogelstein et al. |
| 2004/0253727 A1 | 12/2004 | Harrington et al. |

FOREIGN PATENT DOCUMENTS

WO    WO 2004/061082    7/2004

OTHER PUBLICATIONS

Gallmeier et al.(2007) "Gene-specific selection against experimental Fanconi anemia gene inactivation in human cancer" Cancer Biology & Therapy 6(5):654-660.*
Muller (1999) "Ten years of gene targeting: targeted mouse mutants, from vector design to phenotype analysis" Mechanisms of Development 82(1-2):3-21.*
Marcelo A. Carvalho et al., "Functional Assay for BRCA1 and BRCA2", Int. J. Biochem. Cell Biol., vol. 39(2), pp. 298-310, Aug. 18, 2006.
Tomas Hucl et al., "A Syngeneic Variance Library for Functional Annotation of Human Variation: Application to BRCA2", Cancer Res., Vo. 68(13), pp. 5023-5030, Jul. 1, 2008.
Sergey G. Kuznetsov et al., "Mouse Embryonic Stem Cell-Based Functional Assay to Evaluate Mutations in BRCA2", Nature Medicine vol. 14(8), pp. 875-881, Jul. 6, 2008.

* cited by examiner

*Primary Examiner* — Tracy Vivlemore
*Assistant Examiner* — Karen S Weiler
(74) *Attorney, Agent, or Firm* — Mintz Levin Cohn Ferris Glovsky and Popeo, P.C.; Peter F. Corless, Esq.; Daniel W. Clarke

(57) ABSTRACT

Provided herein are compositions and methods for assaying the deleteriousness of putative loss-of-function mutations, especially in genes known to be or suspected of being tumor-suppressor genes. The invention includes syngeneic variance libraries and methods of construction and use of syngeneic variance libraries.

9 Claims, 5 Drawing Sheets

FUNCTIONAL ASSAY FOR IDENTIFICATION OF LOSS-OF-FUNCTION MUTATIONS IN GENES

RELATED APPLICATIONS

This application is the U.S. National Phase Application, pursuant to 35 U.S.C. §371, of PCT International Application Serial No. PCT/US2008/010233, Filed Aug. 28, 2008, designating the United States and published in English on Mar. 12, 2009 as publication WO 2009/032185, which claims priority to U.S. Provisional Patent Application Ser. Nos. 60/966,404 and 61/067,610 filed on Aug. 28, 2007 and Feb. 29, 2008, respectively, all of which applications are incorporated by reference herein in their entirety.

STATEMENT OF RIGHTS TO INVENTIONS MADE UNDER FEDERALLY SPONSORED RESEARCH

This work was supported in part by the NCI grants CA62924 and CA88843. The government has certain rights in the invention.

SEQUENCE LISTING

The instant application contains a Sequence Listing which has been submitted via EFS-Web and is hereby incorporated by reference in its entirety. Said ASCII copy, created on Aug. 28, 2008, is named 82363_71699.ST25.txt and is 4.11 megabytes in size.

BACKGROUND OF THE INVENTION

It generally accepted that cancer results from the accumulation of sequential mutations in a cell that confer a selective growth advantage to the cell. The tumor is a clonal expansion of the cell containing the mutations, and cells within the tumor likely accumulate further mutations during proliferation. This accumulation of mutations results in genetic instability that leads to uncontrolled growth due to hyper-proliferation or insufficient apoptosis. The loss of genomic stability occurs early in the process of carcinogenesis and represents a key molecular step in the development of cancer by providing a permissive environment in which further mutations can accumulate.

Mutations that result in a gain of function (e.g., activation of Ras by mutation at amino acid 12) can result in the development of cancer alone. However, mutations that result in genomic instability are often loss-of-function mutations in genes responsible for DNA repair, cell division cycle checkpoints, cell motility, transcriptional regulation, and apoptosis. These genes are often called tumor-suppressor genes. A large number of genes identified in screens to be involved in cancer have undefined or incompletely defined relationships uniting their structure with their biological function (e.g., BRCA2), making it difficult, if not impossible, to determine which mutations, if any, are deleterious to gene function. Loss of a first allele does not lead directly to cancer, but makes the cell susceptible to increasingly severe consequences upon acquisition of further mutations. For example, loss of a second allele on the same gene, or mutation of another gene in a pathway in which the first mutation occurred can lead to loss of cell cycle control.

Although some cancers have a strong hereditary component, the large majority of cancers are not associated with a specific genetic predisposition. Moreover, a large number of familial cancers associated with loss-of-function of genes (e.g., BRCA1, BRCA2, MLH1, MSH2) may not manifest overt disease until after the individual has produced children. Similarly a number of other later onset diseases that may have a genetic component (e.g., alpha- or beta-synuclein mutations or APO-E variants in Alzheimer's disease, HTT mutations in Huntington disease, and late-onset forms of diseases more commonly known as affecting the young, such as Tay Sachs or cystic fibrosis, that do not manifest overt disease until the individual has produced children.

Large scale analyses have been performed on tumor samples to identify mutations associated with cancer (e.g., Dutt et al., *Curr. Opin. Oncol.* 2007. 19:43-49; Greenman et al., *Nature* 2007. 446:153-158; Ottini et al., *Ann. Oncol.* 2006. 17:vii97-vii102; Sjöblom et al., *Science*, 2006. 314: 268-314; Lea et al., *Carcinogenesis* 2007. 28:1851-1858, each incorporated herein by reference). However, such analyses were performed on tumor samples or cancer cell lines which have accumulated multiple mutations. For example, analysis of 13,023 genes in 11 breast and 11 colorectal cancers by Sjöblom revealed that individual tumors accumulate about 90 mutant genes, but that only a subset of the mutations contribute to the neoplastic process. Mutations that were germline variants (i.e., present in the patients' genomes at birth) but resulting in no changes in the amino acid sequence of the protein encoded, as well as germline variants identified from the published human sequence present in SNP databases or in two control samples, were disregarded as not being related to cancer. Using these stringent criteria, 189 genes were identified that were mutated with a significant frequency, with an average of 11 genes mutated per tumor. However, despite the identification of such genes and mutations, such a screen does not identify which mutations are deleterious, causing a change of function in the gene product, or are benign. The screens are also not useful for determining which of the less common tumor mutations or which of the germline variants result in an alteration of function that results in a greater susceptibility to disease in a subject as compared to the general population.

SUMMARY OF THE INVENTION

The invention provides a method for functional analysis and classification of potential loss of function mutations in genes putatively associated with disease. The invention further provides reagents such as libraries and kits for use in the methods of the invention.

The invention provides methods for classifying the relative deleteriousness of a mutation in a nucleic acid sequence of a gene to a mammalian cell (e.g., deleterious, benign, or somewhere therebetween) using mammalian cells having only a single functional copy of a first gene and transforming the cells with a nucleic acid sequence from a second gene having one or more the mutations to be classified. The nucleic acid for transformation into the cell includes sequences to allow for recombination of the transformed nucleic acid sequence into a functional gene of the cell, although in certain embodiments, recombination into a non-functional gene may be possible. The frequency of recombination of nucleic acid sequence into the genome of the cell is determined, and the relative frequency of recombination of the nucleic acid containing one or more mutations into a functional gene as compared to a control is indicative of the relative deleteriousness of the mutation. The frequency of recombination of the nucleic acid into the functional copy of the gene as compared to the control non-functional copy of the gene can be determined. Alternatively, the frequency of recombination of a nucleic acid containing potentially deleterious mutations can be compared to the frequency of recombination of a control wild-type sequence or sequence known to not contain deleterious mutations.

In some embodiments, the nucleic acid with one or more mutations is flanked by sequences to allow recombination with the single functional gene in the cells. In an alternative embodiment, the nucleic acid with the mutations is flanked by sequences to allow recombination with a gene other than the single functional gene present in the cell. The number of mutations present in the nucleic acid for recombination can be, for example, at least 1, 2, 3, 4, 5, 10, 15. 20, 25, 30, 35, 40, 45, or 50 mutations. The number of mutations is limited only by the requirement that the nucleic acid be able to recombine with the genome of the cell into which it is transformed. In some embodiments, one or more portions of the non-functional copy of the gene corresponding to the single functional copy of the gene are present in the cells. In other embodiments, the non-functional copy of the gene is substantially deleted from the cells. In some embodiments, portions of the non-functional gene are deleted to prevent recombination of the nucleic acid containing mutations into the non-functional copy of the gene.

The methods of the invention are preferably for use with loss-of-function mutations or mutations that result in a recessive phenotype. Such mutations cannot typically be detected by functional assays due to the presence of a wild-type or at least fully functional gene. Two mutations that alone would not be deleterious to the cell may be deleterious when in combination with each other. The methods of the invention are useful, for example, for the characterization of tumor-suppressor genes. The methods are also useful for the characterization of genes involved in diseases that have relatively late onset, or onset after individuals have reached child bearing age. The methods allow for the characterization of natural variants in the population or artificially generated mutations as deleterious or benign.

In some embodiments, the invention provides methods for the use of a library of cells each containing a different single functional copy of a gene. Such a library of cells is transformed with a nucleic acid construct for recombination. In an embodiment, the cells for use in the methods of the invention are somatic cells. In an embodiment, the cells are human cells.

In some embodiments, the cells including a single functional copy of a gene are transformed with a library of constructs including different genes, or different mutations in a single gene. In some embodiments, the methods are performed iteratively to identify mutations that are deleterious to the cell. For example, if a nucleic acid for recombination includes 50 mutations and has a very low recombination frequency, indicating one or more deleterious mutations, a series of nucleic acid constructs including fewer muations can be generated (e.g., 10 nucleic acids each with about 5 mutations). The recombination frequency of the new constructs can be determined to identify deleterious or benign mutations. Deleterious mutations can be further characterized by generation of constructs with single mutations.

The invention provides methods for characterization of mutations anywhere in the genomic sequence of the gene or genes of interest. For example, mutations can be in any region of the gene, for example in an intron, an exon, a 3'-UTR, 5'-UTR, transcriptional regulatory region, translational regulatory region, or a region at a junction between two of the juxtaposed regions.

The methods of the invention further include functional testing of cells in which the nucleic acid construct containing the mutations has recombined into the genome of the cell containing only a single functional copy of the gene. Functional assays include, but are not limited to, drug or agent sensitivity assays, radiation sensitivity assays, kinase assays, migration assays, proliferation assays, apoptosis assays, chromosome counting assays, nutrient sensitivity assays, transcription assays/reporter construct assays, DNA repair assays, or any combination thereof (e.g., apoptosis assays after exposure to drugs).

The invention further provides cells, preferably somatic cells, preferably human somatic cells having a single functional copy of a first gene transformed with a nucleic acid construct have a sequence from a second gene having at least one mutation to be classified as deleterious flanked by nucleic acid sequences to allow recombination of the nucleic acid sequence from the second gene into a functional gene of the genome of the cell. Such cells include cells in which the construct has been transformed into the cells in which recombination may or may not have taken place. That is, the construct can be present in the cell or incorporated into the genome of the cell, or a combination thereof. In some embodiments, the nucleic acid sequence from a second gene having at least one mutation is a fragment of the first gene that is present as a single functional copy in the cell. In other embodiments, the nucleic acid sequence from a second gene comprising a mutation is not a fragment of the first gene that is present as a single functional copy in the cell. In an embodiment, mutation of the first gene and the second gene is expected to result in a loss of function of the gene in which the mutation is present. In an embodiment, the first gene, or the second gene, or both genes are suspected of being tumor-suppressor genes.

In some embodiments, the cells contain a non-functional copy of the first gene that is present as a single functional copy in the genome of the cell. In some embodiments, at least one of the flanking sequences in the nucleic acid construct is not present in the non-functional copy of the first gene in the mammalian cell, preventing recombination of the nucleic acid construct with the non-functional copy of the cell. In a preferred embodiment, the non-functional copy of the gene in the cell is disrupted in a way to prevent correction of the mutation by recombination with the construct.

The invention provides libraries of nucleic acid constructs having a group of nucleic acid members. The library members include a nucleic acid sequence of a gene flanked by sequences to allow for recombination with a genomic sequence of a functional gene. The members of the library preferably include at least one mutation as compared to a wild-type sequence of the gene. Members of the library can include for example, at least 1, 2, 3, 4, 5, 10, 15. 20, 25, 30, 35, 40, 45, or 50 mutations. Members of the library can include wild-type sequences to act as controls. The mutations present in the sequences in the library can correspond to known, naturally occurring mutations and variations within the genome (either SNPs or VUS), or can be generated randomly or by site directed mutagenesis. The specific sites and numbers of mutations is not a limitation of the compositions and their methods of use herein. For example, mutations can be in any region of the gene, for example in an intron, an exon, a 3'-UTR, 5'-UTR, transcriptional regulatory region, translational regulatory region, and a region at a junction between two juxtaposed regions. The number and sites of mutations are limited only by the variation that is tolerated while allowing for recombination of the nucleic acid sequence with the genome of the cell. Therefore, sufficient regions of homology must be present to allow for recombination.

The invention further provides an isolated population of mammalian cells, preferably somatic cells, preferably human cells, wherein the genome of the cells includes a single functional copy of a first gene in the genome, and the cell further includes a nucleic acid construct comprising a nucleic acid sequence from a second gene comprising at least one mutation flanked by nucleic acid sequences to allow recombination within a functional gene of the genome of the cell. For example, the nucleic acid sequence can include at least 1, 2, 3, 4, 5, 10, 15. 20, 25, 30, 35, 40, 45, or 50 mutations. Such cells include cells in which the construct has been transformed into the cells in which recombination may or may not have taken place. That is, the construct can be present in the cell or incorporated into the genome of the cell, or a combination thereof. In some embodiments, the nucleic acid construct comprises a library of nucleic acid constructs. In some embodiments, the second gene is the same as the first gene. In other embodiments, the second gene is not the same as the first gene. The mutations present in the sequences in the library can correspond to known, naturally occurring mutations and variations within the genome, or can be generated randomly or by site directed mutagenesis, and the mutations can be present in any portion of the genomic sequence. In some embodiments, at least one of the flanking sequences is not present in a non-functional copy of the first gene in the mammalian cell, preventing recombination of the nucleic acid sequence with the non-functional copy of the gene. In an embodiment, mutation of the first gene and the second gene is expected to result in a loss of function of the copy of the gene. In an embodiment, the first gene, or the second gene, or both genes are suspected of being tumor-suppressor genes.

The invention further provides method for screening for a mutation in a nucleic acid sequence as deleterious to a mammalian cell using cells having a single functional copy of a first gene and transforming the cell with a library of nucleic acid construct members having a sequence with at least one mutation to be screened flanked by nucleic acid sequences to allow recombination with the genome of the cell in a functional gene. The frequency of recombination of nucleic acid sequence into the genome of the cell is determined, and the relative frequency of recombination of the nucleic acid containing one or more mutations into a functional gene as compared to a control is indicative of the relative deleteriousness of the mutation. The frequency of recombination of the nucleic acid into the functional copy of the gene as compared to the non-functional copy of the gene can be determined. Alternatively, the frequency of recombination of a nucleic acid containing potentially deleterious mutations can be compared to the frequency of recombination of a wild-type sequence or sequence known to not contain deleterious mutations. For example, the nucleic acid sequence can include at least 1, 2, 3, 4, 5, 10, 15. 20, 25, 30, 35, 40, 45, or 50 mutations. In some embodiments, the first gene and the second gene are the same. In other embodiments, the first gene and the second gene are not the same. The invention provides methods for characterization of mutations anywhere in the genomic sequence of the gene or genes of interest. For example, mutations can be in any region of the gene, for example in an intron, an exon, a 3'-UTR, 5'-UTR, transcriptional regulatory region, translational regulatory region, and a region at a junction between two juxtaposed regions. The methods of the invention are particularly useful for the characterization of loss-of-function mutations in one or more genes.

The methods of the invention further include functional testing of cells in which the nucleic acid construct containing the mutations has recombined into the genome of the cell containing only a single functional copy of the gene. Functional assays include, but are not limited to, drug or agent sensitivity assays, radiation sensitivity assays, kinase assays, migration assays, proliferation assays, cell cycle assay, apoptosis assays, chromosome counting assays (i.e., ploidy determination), nutrient sensitivity assays, transcription assays/reporter construct assays, DNA repair assays, or any combination thereof (e.g., apoptosis assays after exposure to drugs).

The invention provides a database including information regarding the significance of variants in sequences and their relative deleteriousness to a cell, particularly mutations identified and/or characterized using the methods provided herein.

The invention further provides kits for practicing the methods herein. For example, a kit can include a library of cells or a library of nucleic acid constructs with instructions for use. The kits can further include control cells or nucleic acid sequences. Kits can be packaged in appropriate containers.

DEFINITIONS

"Loss-of-function" as used herein refers to a reduction or elimination of the normal activity of a gene or gene product. Loss of activity can be due to a decrease in transcription and/or processing of the RNA, a decrease in translation, stability, transport, or activity of the gene product, or any combination thereof.

As used herein, "deleterious" is understood as harmful, often in a subtle or unexpected way. For example, a deleterious mutation may not result in any overt phenotypic change (e.g., cell morphology, doubling time, maintenance of cell cycle checkpoints, DNA repair, alterations in motility, etc.) when present alone in the cell, however, a deleterious mutation can increase the susceptibility of the cell to genomic instability, or result in an overt phenotypic change when present in combination with a mutation in the second copy of the gene in the cell, or with one or more other gene mutations in the cell which, alone, do not result in any overt phenotypic change in the cell. Genomic instability can manifest, for example, as an increased mutation accumulation, aneuploidy, apoptosis, and mitotic catastrophe.

As used herein, "benign" or "neutral" is understood as a mutation that does not threaten health or life; especially: not becoming cancerous or having no significant effect on tissue function. For example, benign mutations do not alter the function of the gene or gene product e.g., a silent mutation in the coding sequence that does not alter the amino acid sequence of the final protein, mutations of intron or untranslated sequences that do not alter splicing or processing of the mRNA transcript.

As used herein, "hypomorphic" is understood as a mutation that reduces, but does not completely eliminate, the function of a gene.

As used herein, the terms "deleterious" and "benign" are understood as being the two ends of a continuum encompassing the natural complexity of human genetics. For example, specific mutations of p53 or retinoblastoma gene (Rb) in a subject typically result in onset of cancer in the first or second decade of life and with multiple, independent tumors/types of cancer arising during the lifetime of the subject, whereas mutations in BRCA1 and 2 tend to result in later onset of cancer (in the late third decade of life, or later), with often with only one tumor/type of cancer arising during the lifetime of the subject. Therefore, a deleterious BRCA1 or 2 mutation can be less obvious in a clinical setting and would be considered less deleterious than a deleterious p53 or Rb mutation, but would not be considered benign As another example, a known "permutation" in the APC gene is not in itself dysfunctional, but is more prone to additional mutation and thus an increased risk of colorectal cancer, it likewise could not be considered benign.

As used herein, "frequency of recombination" or the "frequency of recombination into a functional gene" of a specific gene segment during an experimental investigation is the number of recombination events of a specific gene fragment containing a mutation relative to the number of recombination events expected to be observed or observed for a control sequence not including a deleterious mutation (e.g., a control sequence may be used that preferably includes one or more silent mutations to allow for detection of its recombination into the genome of the cell). For example, we can consider a hypothetical gene whose function is required for cell survival. If two possible sites for recombination in the cell are possible, one in the wild-type copy of the gene and one in an inactive mutated copy of the gene, and the insertion of an introduced sequence containing a new, different mutation into both the wild-type and mutant copy of the gene (i.e., the recombination frequency) is observed to be nearly the same, the new mutation is concluded to be neutral. However, if insertion (recombination) of the gene fragment including the new mutation into the inactive mutated copy of the gene is highly preferred, the new mutation in the gene fragment is concluded to be deleterious to the cell. Similarly, the recombination frequency of a gene fragment including a mutation can be compared to the recombination of a comparable gene fragment not including the mutation. A substantial reduction in the number of recombinants generated using the sequence including the mutation is indicative of a deleterious mutation. For example, the frequency of recombination of a gene fragment containing a potentially deleterious mutation may be about 75%, 50%, 25%, 10%, 5%, 1%, 0.5%, 0.1%, 0.01%, 0.001%, or less, including none detectable, of that found when testing a fragment not containing a deleterious mutation. In a preferred embodiment, the control sequence is about the same size and will insert into the genome of the cell at about the same locus as the gene segment containing the potentially deleterious mutation. The use and selection of appropriate controls is within the ability of those skilled in the art.

A "tumor-suppressor gene", as used herein, is a gene that when mutated to functionally alter or inactivate the gene product results in an increased susceptibility to genomic instability and cancer. Mutation of a tumor-suppressor gene often results in a loss-of-function such that the gene product does not induce genomic instability alone, but instead allows for cell growth and division to occur without the proper controls. Tumor-suppressor genes, as used herein, have a number of functions within the cell including DNA-repair, cell cycle checkpoints, transcriptional regulation, cell adhesion and motility, signal transduction, transport, metabolism including RNA metabolism, and intracellular trafficking. (The DNA-repair genes and other genes involved in genome maintenance are sometimes considered as a distinct subset, but herein we will include them among the tumor-suppressor genes.) There are also many tumor-suppressor genes for which specific functions have not been assigned. Some tumor-suppressor genes are associated with specific cancers, whereas others are not. Tumor-suppressor genes and genes suspected of being tumor-suppressor genes include, but are not limited to, BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, and LKB1/STK11. GenBank and SEQ ID NOs are provided in Table 2. Genes suspected of being tumor-suppressor genes include genes that are known tumor-suppressor genes.

Other genes for use in the method of the invention, some of which may be suspected of being tumor-suppressor genes include, but are not limited to ATM, ATR, FANCD2, FANCA, FANCB, FANCC, FANCD1, FANCE, FANCF, FANCG, FANCL, FANCM, FAAP100, FLNB, TMPRSS6, RAPH1 1.4 PKHD1, CNTN4, MYH1, COL11A1, PCDHB15, ADAMTSL3, CRL1, SPTAN1, DNAH9, CMYA1, OBSCN, HAPLN1, DBN1, OBSCN, MACF1, ADAMTS18, MGC33407, TECTA, COL7A1, SYNE2, MMP2, MAP2, ADAM12, MAGEE1, NRCAM, TTLL3, GSN, CDH10, COL19A1, EVL, CDH20, SULF2, SEMA5B, ADAM29, BGN, CNTN6, ITGA9, CSMD3, ICAM5, THBS3, ADAMTS15, VEPH1, PFC, PRPF4B, APC, PTPRD, SBNO1, GAB1, CENTG1, KRAS, MCP, DNASE1L3, ARHGEF4, MAP3K6, RAP1GA1, NALP8, APC2, GUCY1A2, PTPRU, EGFL6, RGL1, STARD8, EPHB6, CD109, AMFR, PPM1E, PTPN14, PHIP, CENTB1, PKDREJ, IRTA2, GNAS, GPNMB, CNNM4, RASGRF2, RET, INHBE, ALS2CL, MTMR3, P2RY14, FLJ10458 L. RASAL2, LGR6, CHD5, ZFP64, TP53, ZNF442, FLJ13479, CIC, ZNF569, SMAD3, SIX4, KEAP1, EHMT1, MLL3, EYA4, KIAAO934, HOXA3, ZFYVE26, TBX22, PKNOX1, LRRFIP1, TCF1, BCL11A, MKRN3, GLI1, HDAC4, ZNF318, TCF7L2, RFX2, MYOD1, HIST1H1B, ZCSL3, NCOA6, RUNX1T1, ATP8B1, ABCB8, ABCB10, ABCA1, C6orf29, CUBN, KPNA5, SCNN1B, SLC29A1, GRIN2D, ABCA3, NUP133, SCN3B, HDLBP, SLC9A2, P2RX7, NUP214, SLC6A3, KCNQ5, ACADM, NCB50R, PHACS, UQCRC2, PRPS1.ASL, XDH, ACSL5, CYP1A1, GALNT5, GALNS, OTOF, PLEKHA8, KTN1, SYNE1, PRKD1, LRBA, LOC283849, GGA1, SEC8L1, LRP2, AEGP, SORL1, SDBCAG84, C14orf155, RNU31P2, KIAA0427, SFRS6, SP110, C22orf19, DDX10, FLJ40869, SERPINB1, FBXW7, K6IRS3, UHRF2, CD248, MRE11A, LMO7, ERCC6, KIAA1632, KIAA0999, C10orf137, KIAA1409, MGC24047, LOC157697, and C15orf2.

As used herein, "DNA repair" refers to a collection of processes by which a cell identifies and corrects damage to the DNA molecules that encode its genome. In human cells, both normal metabolic activities and environmental factors such as UV light and radiation can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome, which affect the survival of its daughter cells after it undergoes mitosis. Consequently, the DNA repair process is constantly active as it responds to damage in the DNA structure. Disruption of DNA repair results in chromosomal instability and aneuploidy which frequently results in abnormal cell division, mutation accumulation, mitotic catastrophe (i.e., cell death), or cell cycle checkpoint failure resulting in apoptosis.

Loss of function of DNA repair pathways or cell cycle checkpoints can result in double-strand breaks (DSBs), in which both strands in the double helix are severed, are particularly hazardous to the cell because they can lead to cell death or genome rearrangements. Two major mechanisms exist to repair DSBs: non-homologous end joining (NHEJ) and recombinational repair (also known as template-assisted repair or homologous recombination repair).

As used herein, a "cell cycle checkpoint" is a series of tests or evaluations performed by the cell that pause the cell cycle and gives the cell time to repair the damage before continuing to divide. DNA damage checkpoints occur at the G1/S and G2/M boundaries. An intra-S checkpoint also exists. Checkpoint activation is controlled by two master kinases, ATM and ATR. ATM responds to DNA double-strand breaks and disruptions in chromatin structure, whereas ATR primarily responds to stalled replication forks. These kinases phosphorylate downstream targets in a signal transduction cascade, eventually leading to cell cycle arrest. A class of checkpoint mediator proteins are also required for transmitting the checkpoint activation signal to downstream proteins to promote or inhibit progress through the cell cycle.

p53 is an important downstream target of ATM and ATR, as it is can induce apoptosis or aid cell cycle arrest to prevent further injury following DNA damage. At the G1/S checkpoint, p53 functions by causing arrest. At G2/M checkpoint p53 maintains the arrested state.

Inherited mutations that affect DNA repair genes are strongly associated with high cancer risks in humans. Hereditary nonpolyposis colorectal cancer (HNPCC) is strongly associated with specific mutations in the DNA mismatch repair pathway. BRCA1 and BRCA2, two mutations conferring a hugely increased risk of breast cancer on carriers, are both associated with a large number of DNA repair pathways, especially crosslink repair and homologous recombination.

As used herein, a "transcription factor" is a protein that binds to specific sequences of DNA using DNA binding domains and is part of the system that controls the transcription of genetic information from DNA to RNA.

Transcription factors perform this function alone, or by using other proteins in a complex, by increasing (as an activator), or preventing (as a repressor) the presence of RNA polymerase, the enzyme which activates the transcription of genetic information from DNA to RNA. Many transcription factors, especially some that are oncogenes or tumor-suppressors, help regulate the cell cycle and, as such, determine how large a cell will get and when it can divide into two daughter cells. One example is the Myc oncogene, which has important roles in cell growth and apoptosis. Many transcription factors are tumor-suppressor genes or oncogenes, and thus mutations or aberrant regulation of them are associated with cancer. For example, Li-Fraumeni syndrome is caused by mutations in the tumor-suppressor p53. Other transcription factors associated with cancer and/or believed to be tumor-suppressor genes include, but are not limited to SMAD2 and SMAD4.

"Apoptosis" refers to an active process of programmed cell death, which occurs normally during growth and development and also under conditions of cellular damage or stress; it is distinguished from necrosis, which is not an active process on the part of the dying cell. Apoptosis is a result of signal transduction cascades activated in the cell, for example by failed cell cycle checkpoints or by alterations in extracellular signaling, e.g., loss of growth factor receptor binding of a ligand such as a growth factor.

As used herein, "signal transduction pathway" refers to any process by which a cell converts one kind of signal or stimulus into another. Most processes of signal transduction involve ordered sequences of biochemical reactions inside the cell, which are carried out by enzymes, resulting in a signal transduction pathway.

Mutation of multiple genes within a single signal transduction pathway can result in a synthetic lethal mutation, wherein a viable cell can contain a mutation in either one gene or the other, but not both. Combination of the mutations in a single cell results in senescence or death of the cell.

As used herein, an organism is referred to as being "homozygous" (basically meaning of the same alleles) at a specific locus when it carries two identical copies of the gene affecting a given trait on the two corresponding homologous chromosomes (e.g., the genotype is PP or pp when P and p refer to different possible alleles of the same gene). Such a cell or such an organism is called a homozygote. A homozygous dominant genotype occurs when a particular locus has two copies of the dominant allele (e.g. PP). A homozygous recessive genotype occurs when a particular locus has two copies of the recessive allele (e.g. pp). Herein single alleles are referred to not as "homozygous" as "hemizygous" is the more instructive term for such a state.

A "functional assay" is a method to detect the activity of a gene, protein, or cell in response to a stimulus or insult. The specific functional assay performed depends on the specific mutation or mutations incorporated into the genome of the cell. Functional assays include, but are not limited to, kinase assays, transcription assays using, for example, reporter constructs, proliferation assays, apoptosis assays, migration/chemotaxis assays, nutrient sensitivity assay, agent (e.g., drug, chemotherapeutic agent, mutagen) or radiation sensitivity assays, nucleic acid-binding assay or protein-binding assay, all of which are within the ability of those of skill in the art.

As used herein, "hemizygous" describes an individual or cell which has only one full allele of a gene or chromosome segment rather than the usual two. A hemizygote refers to a cell or organism whose genome includes only one full allele at a given locus, whether the allele is wildtype or mutant. Therefore, a diploid hemizygous individual or cell can be P-null or p-null. For organisms where the male is heterogametic, such as humans, it refers in particular to X-linked genes, since males normally possess only one X-chromosome. They are hemizygous for (nearly) all genes that are located on the X-chromosome. An individual can also be hemizygous at a single locus due to genetic rearrangements and/or targeted deletions. When a rearrangement or large deletion of a chromosome renders one of the original two alleles so incomplete as to practically and irreversibly lose all potential function, herein it will be referred to as a hemizygous state.

As used herein, "heterozygosity" refers an individual having two different alleles of a gene. Heterozygous as used herein can refer to an individual having a dominant and a recessive allele of a gene, e.g., Pp, or to an individual who is hemizygous for a locus, e.g., P-null or p-null. Heterozygous can also refer to an individual or a cell that includes a mutation, e.g., point mutation, mis-sense mutation, non-sense mutation, deletion, introduced at a specific site. In population genetics, it is commonly extended to refer to the population as a whole, i.e. the fraction of individuals in a population that are heterozygous for a particular locus.

As used herein, "loss of heterozygosity" refers to the process of mutation (e.g., point mutation, insertion, deletion, translocation, copy number changes) by which a heterozygous somatic cell becomes homozygous or hemizygous for the allele, for example a mutated tumor-suppressor gene.

As used herein, having a "single functional copy" of a gene refers to a cell in which all of the copies of a particular gene except one is inactivated by mutation, either by manipulation using molecular biology techniques, or naturally occurring mutation, or both. Primary cells, for example from transgenic animals, may include only a single functional copy of a gene, e.g., heterozygous or hemizygous for a gene knockout or disruption. Although mammalian cells are typically diploid, it is within the scope of the invention to use cell lines that are immortalized that include more than two copies of a gene of interest; therefore, more than one copy of the gene may need to be disrupted to make the cell line include only a single copy of the gene. Methods of determining copy number of a gene for example using Southern blot or quantitative PCR is well within the ability of those of skill in the art.

As used herein, "gene" refers to the genomic sequence including introns, exons, control regions, 3'- and 5'-untranslated regions. A cDNA is a copy of the mRNA which is translated into the protein after splicing and other post-transcriptional processing events.

As used herein, an "exon" is a nucleic acid sequence that is represented in the mature form of an RNA molecule after a) portions of a precursor RNA, introns, have been removed by cis-splicing or b) two or more precursor RNA molecules have been ligated by trans-splicing. The mature RNA molecule can be a messenger RNA or a functional form of a non-coding RNA such as rRNA or tRNA. Depending on the context, exon can refer to the sequence in the DNA or its RNA transcript.

As used herein, "UTR," which stands for "untranslated region," refers to either of two sections on each side of a coding sequence on a strand of mRNA. If it is found on the 5' end, it is called the 5' UTR, or if it is found on the 3' end, it is called the 3' UTR. The untranslated regions typically include control regions involved in translation, RNA targeting, and post-transcriptional processing.

The term "intron," derived from the term "intragenic region" and also called intervening sequence (IVS), are DNA regions in a gene that are not translated into proteins. These non-coding sections are present in precursor mRNA (pre-mRNA) and some other RNAs, and removed by splicing during the processing to mature RNA. After intron splicing, the mRNA consists only of exons, which are translated into a protein. Mutations present in introns are often silent. However, intronic mutations can result in aberrant or alternative splicing.

As used herein, "database" refers to a collection of information, preferably in an electronic searchable format, that includes a specific class of information. For example, the information included in the database can be a list of mutations present in a gene and a scoring of the mutation or site of mutation as to the deleteriousness of the specific mutation or site of mutation, and/or the specific disease associated with the specific mutation or site of mutation.

As used herein, "library" is a collection of nucleic acid sequences, typically corresponding to a specific gene where the members of the library include one or more mutations in the gene as well as to the corresponding "normal" gene or a known, benign SNP of a "normal" gene. A library can include sequences from multiple genes. The nucleic acid sequence members typically contain a fragment of the sequence of the gene, e.g., intron, exon, and/or transcription or translational regulatory region, for example the 3'-UTR, 5'-UTR, or in a region at the junction of two of the juxtaposed regions, for example intron/exon junction or 5'-UTR/exon junction. In an embodiment, the library includes a series of mutations, either generated randomly or by design in a gene known to or suspected of being a tumor-suppressor gene or otherwise associated with cancer. Library members also preferably include sequences that facilitate replication of the library, e.g., plasmid sequences for replication in E. coli, chromosomal sequences in mammalian or yeast cells, in viral vectors, e.g., adenoviral vectors, adeno-associated viral vectors. A library can have essentially any number of members greater than 1, for example about 2, 5, 10, 15, 20, 25, 50, 100, 150, 200, 250, 500, 750, 1000, 1500, 5000, or more.

As used herein, a "nucleic acid fragment of a gene" is a portion of a gene large enough to include a mutation (e.g., 1 nucleotide) that is flanked by regions that allow for recombination of the fragment into the genome of a cell. Regions that allow for recombination into the genome of mammalian cells are at least about 50, 100, 250, 500, 750, 1000, 1500, or 2000 bp on each side of the mutation. Therefore, the overall length of a gene fragment for recombination should be about 100 to 4000, 250 to 4000, 500 to 2000, or 500 to 3000 bp with the mutation relative to the genomic sequence at least about 50, 100, 250, 500, 750, or 1000 bp of nucleotides from the end of the fragment. The portion of the fragment including the mutation need not necessarily be distinct from the flanking regions to allow recombination. The specific length of the nucleic acid fragment used is not a limitation of the methods of the invention as long as the fragment is of an appropriate size to allow for recombination.

The methods herein include recombination into a "functional gene" which is understood as insertion of the nucleic acid fragment into any portion or portions of a gene, e.g., intron, exon, transcriptional/translational control region, 3'UTR, 5'UTR, wherein the "functional gene" encodes a protein that has at least partial function of the wild-type gene, for example at least about 50%, 60%, 70%, 80%, or 90% of the activity of the wild-type gene as determined by standard functional assays for the specific gene type. A "functional gene" can include naturally occurring or artificially inserted mutations or alterations, for example silent mutations that do not alter the coding sequence of the expressed protein, to detect integration of a nucleic acid fragment into the gene, or to determine which strand the gene fragment integrated into.

As used herein, "transforming a cell" is understood as contacting a cell with a nucleic acid under conditions to promote uptake of the nucleic acid into the cell. The method of transfection may be selected based on the cell type into which the nucleic acid is to be introduced. Commonly used transfection methods include electroporation, calcium phosphate precipitation, cationic lipid reagents (e.g., Lipofectamine®, Oligofectamine®), dendrimer reagents. The invention is not limited by the method of transfection. As used herein, a cell transfected with a construct includes cells that contain the construct in the cell, as en episomal plasmid, or integrated into the genome of the cell. It is understood that upon recombination of the fragment into the genome, other sequences included in the originally transfected construct can be lost.

Cell culture is the process by which prokaryotic, eukaryotic or plant cells are grown under controlled conditions. In practice the term "cell culture" refers to the culturing of cells derived from multicellular eukaryotes, especially animal cells. The historical development and methods of cell culture are closely interrelated to those of tissue culture and organ culture.

Cells that are cultured directly from a subject are known as primary cells. With the exception of some derived from tumors, most primary cell cultures have limited lifespan. After a certain number of population doublings cells undergo the process of senescence and stop dividing, while generally retaining viability. Primary cells can be obtained from essentially any source, including transgenic animals.

An established or immortalized cell line has acquired the ability to proliferate indefinitely either through random mutation or deliberate modification, such as artificial expression of the telomerase gene. There are numerous well established cell lines representative of particular cell types. The methods herein can use essentially any cell line, preferably cell lines that are easily transfected by one or more methods. Cell lines for use in the methods of the invention include, but are not limited to cancer cells, near-diploid cancer cell lines having DNA mismatch-repair defects, CHO (Chinese hamster ovary) cells, 293 cells, and cells immortalized with viral transforming proteins or viral infection. Immortalized cell lines are frequently not precisely diploid, and can be aneuploid.

Cells for use in the invention "syngeneic" cells which is understood herein as cells preferably derived from, or being genetically identical. In some embodiments, cells can be derived from similar individuals of the same species especially with respect to antigenic interaction. Syngeneic cells can be cells from the same cell line, primary or immortalized. Syngeneic cells can be derived from isogenic mice or other animals, including transgenic animals.

As used herein, "diploid" is understood as having normal number of chromosomes in a somatic mammalian cell, which is frequently referred to as 2n, with the XX or XY chromosomes being considered as a "pair." During cell cycle phases G2 and M prior to the completion of cell division, the cell has a complement of 4n chromosomes. Gametes have a complement of 1n chromosomes.

As used herein, "aneuploid" is understood as having an abnormal number of chromosomes in a cell (i.e., not diploid in somatic cell, or haploid in gamete). Cells can have double the complement of chromosomes during G2 and M phases of the cell cycle.

The term "single nucleotide polymorphism" or "SNP" is understood as a naturally occurring DNA sequence variation occurring when a single nucleotide—A, T, C, or G—in the genome (or other shared sequence) differs between members of a species (or between paired chromosomes in an individual). For a variation to be considered a SNP, it must occur in at least 1% of the population. SNPS may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed synonymous (sometimes called a silent mutation). If a different polypeptide sequence is produced they are non-synonymous. SNPs that are not in protein-coding regions may still have consequences for gene splicing, transcription factor binding, or the sequence of non-coding RNA.

As used herein, "selecting" is understood as identifying one or more members of a group.

The term "detectable label" is understood as a chemical modification, binding agent, or other tag that can be readily observed, preferably in a quantitative manner, such as a fluorescent tag that has a specific wavelength of absorption and emission to allow detection of the compound associated with the detectable label. Detectable labels include vital dyes for use with living cells wherein the dye has little or no effect on cell viability, growth, and function.

The term "reporter gene" which is typically used in the context of a "reporter construct" which is understood as a coding sequence for a polypeptide that is operably linked to a promoter sequence, typically an inducible promoter. The coding sequence for a polypeptide encodes a polypeptide that can be readily detected, preferably in a quantitative manner, such as alkaline phosphatase, beta-galactosidase, luciferase, green fluorescent protein, etc. Methods to detect the presence of such proteins is well known in the art and can be performed using any of a number of commercially available kits and automated readers. The selection of a reporter gene is a matter of choice.

As used herein, a "normal cell" is a cell that is derived from tissue that does not include any known mutations or disruptions that predispose the cell to a particular disease or disorder.

As used herein, "isolated" or "purified" is understood as being removed from its usual environment or other components with which they are naturally associated. For example, an isolated cell can be removed from an animal and placed in a culture dish or another animal. Isolated is not meant as being removed from all other cells. A group of cells can also be isolated (e.g., bone marrow cells, an organ) from one organism and placed in another organism or in culture. A polypeptide or nucleic acid is isolated when it is about 80% free, 85% free, 90% free, 95% free from other cellular material typically associated with the nucleic acid or polypeptide (e.g., material in a cell in which the nucleic acid or peptide is expressed), or substantially free of chemical precursors or other chemicals when chemically synthesized. An "isolated polypeptide" or "isolated polynucleotide" is, therefore, a substantially purified polypeptide or polynucleotide, respectively. Alternately an isolated nucleic acid or polypeptide may be present in a non-native environment for the molecule, e.g., a heterologous cell, tissue, or animal. As used herein, a "homogenously purified" polypeptide or nucleic acid is about 90%, 95%, 98%, or 99% pure and removed from biological or synthetic contamination from the synthesis of the polypeptide or nucleic acid. A homogeneously purified polypeptide or nucleic acid can be present in a buffer or other carrier such as a pharmaceutically acceptable carrier.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, "nucleic acid sequence fragment" or "gene fragment" and the like are understood as a portion of a gene that includes at least about 8, 10, 12, 15, 17, 20, 25, 30, 35, 40, 45, 50, 55, 60, 65, 70, 75, 100, 150, 200, 250, 500 contiguous nucleotides from a full length naturally occurring gene or genomic sequence. A nucleic acid sequence fragment can include one or more mutations, naturally occurring or artificially (e.g., randomly) generated.

As used herein, nucleic acid sequences from "the same gene" and the like are nucleic acid sequences that are fragments of the same genomic sequence and may or may not include mutations or polymorphisms. A nucleic acid sequence from a gene includes fragments of the gene. A fragment from the same gene has at least 80%, 90%, 95%, or more identity with the wild-type sequence of the gene over the length of the fragment.

As used herein, "mutation" or a "gene comprising a mutation" includes alterations in one or more nucleic acids in a genomic sequence, including one or more base changes, deletions, and/or insertions, that result in silent mutations, nonsense mutations, mis-sense mutations, mutations that result in premature stop codons, aberrant splicing, transcription or translation. A gene comprising a mutation can have more than one mutation.

The terms "identical" or percent "identity," in the context of two or more nucleic acids or polypeptide sequences, refer to two or more sequences or subsequences that are the same or have a specified percentage of amino acid residues or nucleotides that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 20 amino acids or nucleotides in length, or more preferably over a region that is about 25-50, 50-100, 100-200, 20-300, 50-500, 50-1000, 500-1000 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Sequence alignments can be used to determine amino acids that are more or less conserved between species. Alteration of non-conserved amino acids is typically has less of an effect on the activity of a polypeptide than mutation of a conserved amino acid. Similarly, more conservative mutations, based on charge and/or size of the amino acid, typically have less of an effect on the activity of a polypeptide. For example a conservative mutation would include substitution of one small, neutral, non-polar amino acid such as alanine, glycine, isoleucine, leucine, proline, and valine for another. Similarly, mutation of a glutamic acid to an aspartic acid, or vice versa would also be considered a conservative mutation. Exchange of phenylalanine, tyrosine, and tryptophan for each other would be considered a conservative mutation. Protein tolerance to random mutations is understood in the art, for example, see Guo et al. (Protein tolerance to random amino acid change. *Proc. Natl. Acad. Sci. USA* 101:9205-9210, 2004, incorporated herein by reference). SNPs or other natural variations associated with disease can be used to identify essential amino acids that do or do not tolerate mutation.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.* 260:2605-2608 (1985); Rossolini et al., *Mol. Cell Probes*, 8:91-98 (1994)). The term nucleic acid is used interchangeably with gene, cDNA, mRNA, oligonucleotide, and polynucleotide.

By "analog" or "derivative" is meant a molecule that is not identical, but has analogous functional or structural features.

By "small molecule" is meant a compound having a molecular weight of no more than about 1500 daltons, 1000 daltons, 750 daltons, 500 daltons. A small molecule is not a nucleic acid or polypeptide.

As used herein, the term "polymerase chain reaction" (PCR) refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

Of the PCR techniques, RT-PCR (Reverse Transcription-PCR), competitive RT-PCR and the like are used for detecting and quantifying a trace amount of mRNA, and show their effectiveness. A real-time quantitative detection technique using PCR has been established (TaqMan® PCR, *Genome Res.*, 6 (10), 986 (1996), ABI PRISM™ Sequence Detection System, Applied Biosystems, incorporated herein by reference).

The use of PCR and methods to design primers and select polymerases to identify single nucleotide changes are well known in the art. For example, the importance of hybridization of the 3' ends of primer sequences to allow for extension is well known. Methods to distinguish genomic sequences that have undergone recombination, or not, are well known in the art, including primer design, and methods are further provided herein.

As used herein, the term "recombinant DNA molecule" as used herein refers to a DNA molecule, which is comprised of segments of DNA joined together by means of molecular biological techniques.

As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

By "detecting" or "detection" and the like is meant the process of performing the steps for determine if an analyte or nucleotide sequence is present, or to determine if a compound, gene, or mutation has an effect, or if a recombination or insertion has taken place, and the like. The amount of analyte present or the effect may be none or below the level of detection of the method.

As used herein "correlating an mutation in a gene with a diagnosis or predisposition to a disease or condition" is understood as detecting a mutation determined to be deleterious (or not) present in a sample from a subject and associating the presence of the specific mutation with an increased incidence or chance of occurrence (or not) of the development of a specific disease or condition, e.g., a specific type of cancer.

By "ameliorate" is meant decrease, suppress, attenuate, diminish, arrest, or stabilize the development or progression of a disease. Amelioration can require administration of more than one dose.

The term "treated," "treating" or "treatment" includes the diminishment or alleviation of at least one symptom associated or caused by the state, disorder, condition, or disease being treated. For example, treatment can be diminishment of one or several symptoms of a disorder or complete eradication of a disorder. Treatment can also include prophylaxis (i.e., prevention). Treatment can result in amelioration of a disease. Treatment and prophylaxis can require administration of more than one dose.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition in addition to detection of a loss-of-function mutation in a gene that makes the subject susceptible to a particular disease or condition.

By "alteration" is meant a change (increase or decrease) in the expression levels or activity of a gene or polypeptide" as detected by standard art known methods (e.g., ELISA, PCR, mass spectrometry based methods, immunohistochemistry, RIA, functional assays). An alteration in activity for example from a gene mutation may only be detectable when present in combination with a second mutation or alteration.

As used herein, "obtaining" is understood as purchase, procure, manufacture, or otherwise come into possession of the desired material.

"Providing," refers to obtaining, by for example, buying or making the, e.g., polypeptide, drug, polynucleotide, probe, and the like, including libraries of nucleic acids or cells having a targeted heterozygous for a mutation or deletion in a gene. The material provided may be made by any known or later developed biochemical or other technique, e.g., standard molecular biology techniques.

The term "subject" includes organisms which are capable of suffering from a disease of interest that could otherwise benefit from detection of a mutation in a gene that can result in a loss of function of the gene, or predispose the subject to a specific disease or condition such that the subject would benefit from screening. The term "non-human animals" of the invention includes all vertebrates, e.g., mammals, e.g., sheep, dog, cow, and primates including non-human primates; e.g., rodents, e.g., mice, and non-mammals, e.g., chickens, amphibians, reptiles, etc. A human subject can be referred to as a patient.

The term "differential" or "differentially" generally refers to a statistically significant different level in the specified property or effect. Preferably, the difference is also functionally significant. Thus, "differential binding or hybridization" is a sufficient difference in binding or hybridization to allow discrimination using an appropriate detection technique. Likewise, "differential effect" or "differentially active" in connection with a therapeutic treatment or drug refers to a difference in the level of the effect or activity that is distinguishable using relevant parameters and techniques for measuring the effect or activity being considered. For example, identification of a specific loss of function mutation can provide an indication of a drug that may be most useful for the treatment of a specific disease (e.g., cells having mutations in a DNA repair gene may be more susceptible to treatment with a drug that induces DNA double strand breaks). Preferably the difference in effect or activity is also sufficient to be clinically significant, such that a corresponding difference in the course of treatment or treatment outcome would be expected, at least on a statistical basis.

As used herein, "antibody" is understood as whole antibodies such as IgG, IgM, IgA, IgD or IgE, or fragments, such as a Fab, F(ab')$_2$, Fv, disulphide linked Fv, scFv, closed conformation multispecific antibody, disulphide-linked scFv, whether derived from any species naturally producing an antibody, or created by recombinant DNA technology; whether isolated from serum, B-cells, hybridomas, transfectomas, yeast or bacteria). Antibodies can be monoclonal or polyclonal. Antibodies can be humanized (e.g., see U.S. Pat. No. 5,565,332, incorporated herein by reference) or otherwise modified to facilitate administration. Antibodies preferably are specific for their target antigen. Preferably an antibody is specific for its target antigen with at least $10^4$-fold, $10^5$-fold, $10^6$-fold specificity as compared to binding to a non-specific antigen as determined, for example, using a competition binding assay.

Techniques for preparing and using antibody molecules are well known to those skilled in the art (see Harlow and Lane (1989) *Antibodies*, Cold Spring Harbor Laboratory, pp. 1-726; O'Brien and Aitken (2002) Antibody Phage Display, Humana Press).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

As used herein, "about" is understood to mean approximately or reasonably close to, and within the tolerances generally accepted in the specific experiment or result, for example within two standard deviations of the mean of a specific result.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. For example, any single point mutation or alteration of the wild-type sequence can be combined with any other mutation or alteration of the wild-type sequence.

Any compositions or methods provided herein can be combined with one or more of any of the other compositions and methods provided herein.

DETAILED DESCRIPTION OF THE INVENTION

Figure 1:
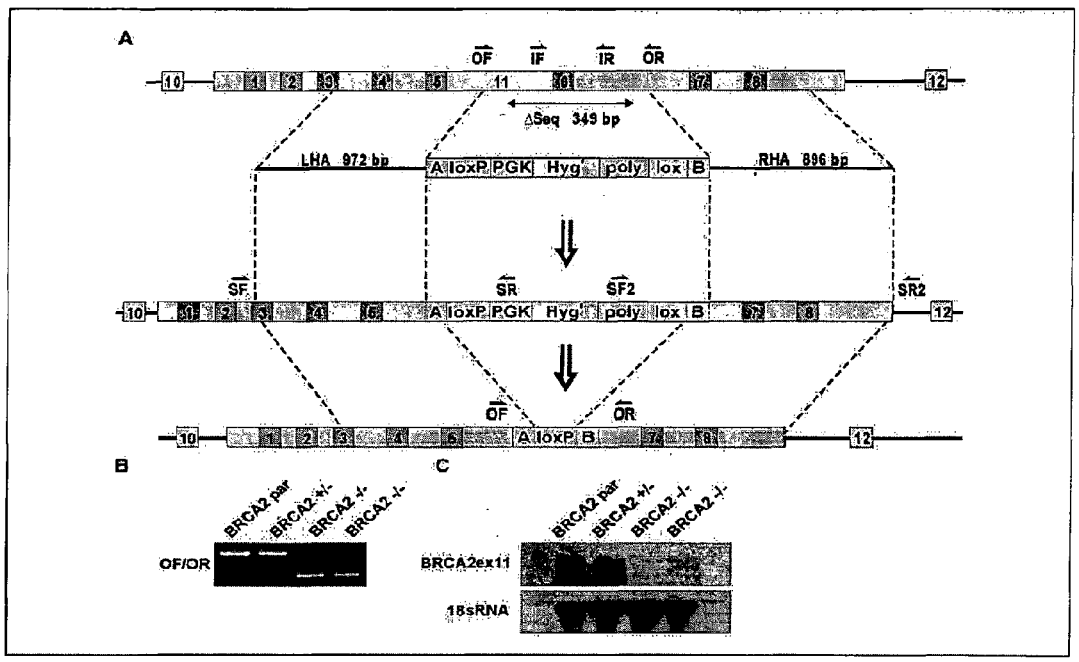
FIG. 1. Structural and functional demonstration of BRCA2 gene disruption. A. Targeting scheme. OF and OR primers outside the deleted sequence. IF and IR primers inside the deleted sequence; SF, SR, SF2, SR2, screening primer pairs; LHA (forward, 5'-GATCAGAAACCAGAAGAATTGC-3' (SEQ ID NO: 36) and reverse 3'-CTGGCTCAATACCA-GAATCAAG-5'(SEQ ID NO: 37)) and RHA (forward, 5'-AGGTTGTTACGAGGCATTGG (SEQ ID NO: 38) and reverse 3'-CGTTTTAGGTGAAGCCTGTTC-5' (SEQ ID NO: 39)), left and right homology arms. Numbers on light background indicate exons, and numbers on dark background indicate BRC repeats. B. PCR detecting the wt and targeted alleles using genomic DNA as a template. C. Northern blot detecting the targeted exon 11 mRNA transcript. D. Structural demonstration of BRCA2 exon 27 targeting. Targeting scheme. OF primer, outside the deleted sequence; IR primers, inside the deleted sequence; SF, SR, SF2, and SR2, screening primer pairs; INF and INR, intron 25 spanning primers; LHA and RHA, left and right homology arms.
Figure 1:
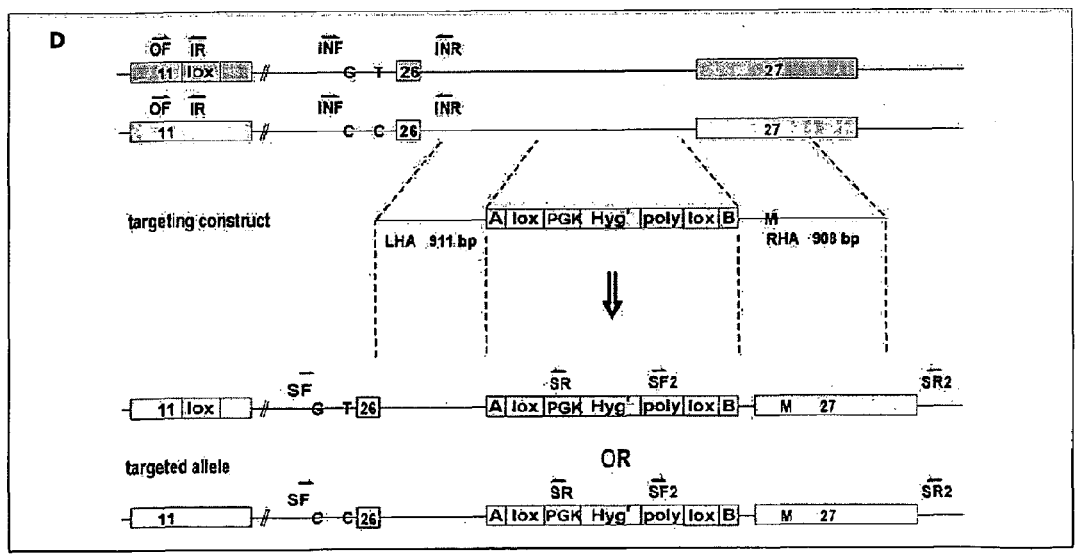

The invention provides compositions, methods, databases, and kits for the identification and characterization of the relative deleteriousness of potential loss of function mutations in genes, for example in suspected tumor-suppressor genes, and for determining susceptibility of a subject to a disease or condition based on the presence of one or more mutations in a gene determined to be deleterious.

The present invention provides a method for distinguishing inactive from active forms of a gene. More specifically, the invention provides a functional assay for distinguishing inactive and active forms of a gene, and the means to classify variants of unknown significance to gene function. By functional evaluation of clones harboring mutations, the invention provides a method to classify sequence variants as deleterious, hypomorphic, or neutral. A hypomorphic mutation reduces, but does not completely eliminate, the function of a gene.

The invention may be used to analyze any gene of interest. In an embodiment, mutation of the gene can results in a loss-of-function of the gene. In an embodiment the gene is a tumor-suppressor gene. For example, the gene is selected from the group consisting of BRCA1, BRCA2, MLH1, MSH2, MSH6, EPHA3, EPHA4, APHB2, 1NI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, and LKB1/STK11

The present invention also provides hemizygous mammalian cell lines comprising a first functional copy (allele) of a gene of interest and a second allele of the same gene with a deleted region abrogating gene function or a region intentionally altered such that the second allele produces a functionally inactive gene product. For example, the gene is selected from the group consisting of BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, and LKB1/STK11

The invention provides methods of introducing into a hemizygous cell line by homologous recombination a gene sequence comprising a single variant of the sequence of the gene of interest or a fragment of a gene of interest. The resulting syngeneic clone differs from the parental line by a single sequence variant. More preferably, the gene is selected from the group consisting of BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, and LKB1/STK11.

The present invention further provides a panel or library of such syngeneic cell lines, a syngeneic variance cell line library. Preferably the syngeneic variant cell line library comprises five or more syngeneic variant cell lines. In the syngeneic variant cell line library, members of the library include genomes that vary at specific, and optionally defined sites. Preferably at specific defined sites within one or more tumor-suppressor genes in the genome, or suspected tumor-suppressor genes in the genome. More preferably, the cell lines of the syngeneic variant library vary at specific, and optionally defined sites within the genomic sequence of a single gene, for example a single tumor-suppressor gene, or the genomic sequence of a suspected tumor-suppressor gene. For example, syngeneic variant library includes cell lines derived from the same source that include a series of mutations at various sites in BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, or LKB1/STK11.

Current means are often inadequate to determine whether a variant of tumor-suppressor genes found upon the genetic study of individual patients is likely to cause an elevated cancer risk. These variants are often termed Variants of Unknown Clinical Significance (UVs, VUSs, etc). Unlike the well-known deleterious mutations of tumor-suppressor genes, such as BRCA2, a large number of variants are, individually, uncommon. Thus the assigned risk for each variant cannot be assessed to a reasonable level of statistical certainty. When a patient is identified to have a UV, it is difficult to provide an unambiguous laboratory interpretive result to the ordering physician, it is difficult to convey to the patient the appropriate genetic counseling, and it is uncertain what should be the appropriate medical management of the patient. The BRCA2 status of the patient, i.e., whether the BRCA2 gene variants are deleterious or nondeleterious (i.e., benign or neutral), are used to advise on cancer risk, frequency and mode of cancer screening, advisability of prophylactic mastectomy or ovarectomy, rationalize a cancer-rich family history, advise on family planning before the birth of offspring, and in an experimental therapeutic setting dictate the selection of specific anticancer drugs thought to be more efficacious when a patient has a deleterious BRCA2 gene. The assignment of a BRCA2 status of "UV" to a patient leads not only to uncertainty as to these issues, but considerable anxiety among the patient and their family members, many of whom are expected to also carry the UV BRCA2 status even if they are not yet tested genetically.

Current epidemiologic techniques to make this decision include the following. If there is considerable past medical experience with other patients having the variant, the statistical association with higher cancer risk will already be known. If the variant has been identified in persons who, in addition, have a known deleterious BRCA2 sequence, the variant is thought less likely to itself be deleterious. If the status of the variant does not track with the disease status among the members of a family having multiple incidents of a BRCA2-related cancer, the variant is also thought less likely to be deleterious. Many variants remain in the UV status even after consideration of these epidemiologic patterns. The cost of testing multiple family members can be prohibitive even when consent and samples can be obtained from a sufficient number of individuals.

Thus, laboratory studies of the biological function of the variant BRCA2 genes have been proposed. This is done because of considerable evidence that the mutations in BRCA2 convey an increased cancer risk only due to the consequential loss of Brca2 protein function. Unfortunately, functional testing cannot be performed directly on the blood cells of the patient, because the patients have two BRCA2 alleles in each normal cell, and the function of the normal allele will mask any deficiencies in the variant allele. On the other hand, the tumor cells of the patient could be studied, for the tumor cells will have lost the normal allele, but such studies are impractical since the patient may not have yet developed cancer, and any cancers that develop cannot be readily obtained in a pure and numerous manner. Moreover, cancer cells typically accumulate mutations as the tumor grows; therefore, it was not possible to determine what mutations were essential to promote the uncontrolled growth of the cells originally, and what mutations were accumulated during the clonal expansion of the initial tumor cell.

Thus, more indirect laboratory techniques have been explored, including the following. Efforts at molecular modeling of the variant sequence use the predicted protein modifications that would be created by each UV, followed by algorithms to score the likelihood of serious protein dysfunction that might result; such efforts have worked when the variant is able to truncate the protein translation (such as nonsense or splice site mutations), but have been unreliable for missense variants. A transgenic mouse or mouse embryonic stem cells can be created that incorporates a mouse analog of the human variant BRCA2 gene, and subsequently studied for Rad51 focus formation, sensitivity to ionizing radiation, or homologous recombination of a plasmid. This assay is prohibitively expensive, and has predominantly been used for obvious deleterious mutations, and is of unclear relevance in studies of subtle human variant sequences because human and mouse proteins differ in their amino acid sequences already. Individual pure clones of the variant or normal BRCA2 cDNA sequences can be introduced into and exogenously expressed in a mammalian cell line, and the cell line is subsequently studied for Rad51 focus formation upon treatment with DNA damaging agents, homologous recombination of a plasmid, or centrosome amplification (Carvalho et al, *J Biochem Cell Biol*, 2007. 39:298-310. Epub 2006 Aug. 18, incorporated herein by reference) in that technique, a number of UVs gave different results in the different assays, leading to confusion as to which of the results to use in assigning clinical risk.

Provided herein are reagents and methods to classify mutations of an interrogated gene as deleterious or benign, or somewhere therebetween, particularly loss of function mutations in loss-of-function genes.

The invention provides a human cell line engineered using DNA recombinant techniques to be genetically constituted as follows: hemizygous for a single native and functional copy of the interrogated gene, and to contain at least one copy at the site of the same gene having been engineered to render it functionally inactive by mutation. A cell containing this resultant allelic arrangement is termed hemizygous for the interrogated gene.

The invention provides introduction of fragments of the interrogated gene, some of which may contain inactivating variants, in a manner leading to homologous recombination of the fragment and replacing a portion of one of the two endogenous gene alleles of the hemizygous cell, one allele (or more, in the case of polysomy wherein the gene may exist in three or more copies) of which was previously engineered to be inactive, one of which had remained native.

The invention includes methods for identification and isolation of recombinant clones including the gene fragment and the inactivated interrogated gene (e.g., tumor-suppressor gene), followed by differential enumeration of the number of hemizygous clones having integrated the fragment into the engineered-inactive and, alternatively, into the native-functional allele of the interrogated gene, to determine the recombination frequency into each the functional allele and the non-functional allele of the same gene.

The recombination frequency of each variant is used to determine the relative deleteriousness of a specific mutation. A variant resulting in live clones having homologous integration only in the engineered-inactive allele, but not in the native-functional allele, would be considered a dysfunctional or deleterious variant, one likely to be pathogenic when inherited by a person. A variant resulting in equal numbers of integrants affecting the engineered and the native alleles would be considered a variant having normal function, one unlikely to be pathogenic (i.e., benign or neutral). Results intermediate between these two scenarios would be assessed statistically to determine whether the results were significantly likely to be intermediate, i.e., not representing a chance departure from either "pure" scenario. Appearance of preferential integration into the active allele could additionally indicate that the mutation promotes cell division or inhibits apoptosis by increasing the apparent rate of proliferation. Similarly, a confidence interval or recombination frequency for the results could be reported, using a spectrum of values from 0 (the emergence of integrants solely into the engineered allele, attributable to dysfunctional variants) to 1 (the equal emergence of the two types of integrants, attributable to a normally functioning variant). The recombination frequency can be expressed as the number of integrants into the normal allele/number of integrants into the non-functional allele.

In an alternative embodiment of the invention, the interrogated gene need not influence cell viability or proliferation, and mutations are classified as deleterious or benign by a biological assay of the recombinant clones containing the mutated fragments. This assay would test for a biochemical property in vivo or in vitro, such as but not limited to alterations in a protein, an RNA species, DNA integrity, activity of a transcriptional reporter, or drug sensitivity.

In another alternative embodiment of the invention, the inactive allele is inactivated in a manner to prevent recombination of the gene fragment with the inactivated gene. In another embodiment, the gene fragment to be tested is a fragment of a gene other than the gene that is inactivated. Such a screen is typically known as a synthetic lethal screen. In such methods, the ratio of integration of the fragment into the functional allele and non-functional allele cannot be compared as preferably only a single site for possible integration exists. The recombination frequency is the frequency of recombination of a gene fragment including a mutation of interest, optionally with other silent mutations/a gene fragment that will result in expression of a wild type gene product (i.e., a gene fragment containing silent mutations, a control sequence) under the same conditions. The use of silent mutations allows for the identification of integrants within the wild type sequence to determine frequency of integration. It is understood that the mutation in the fragment to be tested must be a sufficient distance from the end of the gene fragment to not alter the recombination frequency due to inability to generate stable structures to allow for recombination. Such considerations are routine for those of skill in the art.

In another embodiment of the invention, introduced mutations can be "multiplexed", wherein a mutant allele comprises more than one (optimally three to ten or three to 25 or 3 to 50) discrete variations as compared to the wildtype allele. Using multiplexed variant sequences allows a single recombinant clone to be informative as to the classification of more than one discrete variant. This is especially useful when the fraction of variants exhibiting dysfunction is relatively low.

The variants having a statistically significant departure from a value of 1 for recombination frequency, yet having given rise to at least one integrant into the native-functional allele, can be further studied and potential subgroups of dysfunctional classes assigned functionally according to the residual capabilities of the clones as assessed by tests of gene function. These follow-up tests for example for BRCA2 or other tumor-suppressor genes thought to be involved in DNA repair could include, but are not restricted to, Rad51 focus-formation, sensitivity to anticancer agents, centrosome amplification, and homologous recombination of introduced plasmids. Other tests to assess gene function include, but are not limited to, kinase assays, transcription assays using, for example, reporter constructs, proliferation assays, apoptosis assays, or migration assays, all of which are within the ability of those of skill in the art.

The invention provides kits for the practice of the methods of the invention.

The invention provides syngeneic libraries of dozens or hundreds of engineered cell lines, each line containing a different gene variant. Libraries can included variants of a single interrogated gene or multiple interrogated genes. Libraries can include a mixed population of cells in a single tube, or multiple cell lines each present in a separate tube, or some combination thereof, e.g., a series of mixed populations of cells each mixture including mutations in a single intron, exon, or regulatory control region of an interrogated gene, a series of mixed populations of cells each mixture including mutations in a single interrogated gene.

The invention further provides a database of results obtained by the methods provided herein that lists mutations in interrogated genes and their recombination frequency that correlate with the relative deleteriousness of the specific mutation or combination of mutations. The database can further include, for example, results from other experiments, either in vivo or in vitro, to further characterize the activity of the various mutants.

The scope of natural human genetic variation is now becoming evident but is enormous (Sjoblom, T., et al., 2006 Science 2006. 314, 268-74; Greenman, C., et al., Genetics 2006. 173, 2187-98.). To accurately annotate these variants, and to identify which of them have medical importance through functional assays may be difficult for several reasons. Natural cell lines expressing the variants homozygously are often unavailable and do not allow isogenic experimental controls. Artificially introduced null states can be inviable. For some genes, such as the medically important BRCA2 gene and other tumor-suppressor genes, even the exogenous expression of wild-type gene fragments can cause interference with endogenous gene function (squelching) unless assays are performed with extreme technical care and multiple controls (Esashi, F. et al., Nature 2005. 434, 598-604; Yuan, S. S., et al., Cancer Res. 1999. 59, 3547-51; Davies, A. A., et al., Mol Cell. 2001. 7, 273-82; Wu, K., et al., Cancer Res. 2005. 65, 417-26).

The BRCA2 gene exhibits allelic differences in its sequence among members of the human population. Some of the variants are known to be deleterious, causing inherited susceptibility to breast, ovarian, and other cancer types (King, M. C., et al., Science 2003. 302, 643-6; Goggins, M., et al., Cancer Res. 1996. 56, 5360-4). Unfortunately, in many patients who are tested and have a BRCA2 variant identified, the alteration is subtle, changing a single amino acid (Frank, T. S., et al., J Clin Oncol 2002. 20, 1480-90). For many of these variants, it is not possible to use epidemiological data or laboratory studies of protein function to determine unambiguously nor efficiently whether one should classify the variant as either deleterious or benign.

BRCA2 gene on chromosome 13q12-13 encodes a 3418 amino acid protein. Its sequence reveals only a few clues to its cellular function and thus variation in the sequence is not readily interpreted. The protein's role in DNA repair specifically involves homologous recombination, mediated by its interaction with Rad51 (Connor, F., et al., Nat Genet. 1997. 17, 423-30; Moynahan, M. E., et al., Mol Cell. 2001. 7, 263-72; Wong, A. K., et al., *J Biol Chem*. 1997. 272, 31941-4.). BRCA2 interacts with Rad51 through highly conserved BRC repeats in exon 11 and an interaction domain mapped to exon 27 (Howlett N G, et al., *Hum Mol Genet*. 2005. 14:693-701; Montes de Oca R, *Blood* 2005. 105:1003-1009.). The interaction of Rad51 with exon 27 has been proposed to be down-regulated by CDK-dependent phosphorylation of S3291, which is reduced during S phase and after DNA damage. However, most functional studies of BRCA2 have been hampered by the lack of well-controlled human cancer cellular models. Such absence was in the past overcome by employing methods of considerable technical difficulty.

To accurately annotate sequence variations of the BRCA2 gene in an unambiguous and technically facile model, targeted disruption of BRCA2 exon 11 was performed by homologous recombination, yielding the first available syngeneic human cancer BRCA2 knock-out cell line. Using hemizygous BRCA2 cells, we constructed a library of syngeneic exon 27 genetic variant lines (a SyVaL). By functional evaluation of multiple clones harboring individual mutations, sequence variants were able to be classified as deleterious, hypomorphic, or neutral. A pseudo-phosphorylated BRCA2 variant was also created, replacing the normal gene. The studies disclosed herein support the importance of exon 27 in recombination-mediated DNA repair and the role of serine 3291 in phosphorylation-regulated BRCA2-Rad51 interaction, and provide a proof of concept of the methods of the invention.

The BRCA2 gene exhibits allelic differences in its sequence among members of the human population. Some of the variants are known to be deleterious, causing inherited susceptibility to breast, ovarian, pancreatic, and other cancer types. Unfortunately, in many patients who are tested and have a BRCA2 variant identified, the variant is subtle, changing a single amino acid of the BRCA2 protein. For most of the BRCA2 variants, it is not possible to use epidemiologic data or laboratory studies of protein function to determine unambiguously nor efficiently whether one should classify the variant as either "deleterious" or "benign".

Provided herein is a database that provides an unambiguous numerical functional assessment and interpretation of individual variant alleles, as measured along a continuous spectrum of "deleterious" to "benign". That is, a variant may be classified within the database as belonging to one of these extremes, or as a numerical value intermediate between "deleterious" and "benign".

This database corresponds also to a library, from which it is derived. The library comprises a sizable panel of cell lines derived by recombinant DNA engineering from a heterozygous cell line having only a single functional allele of the gene to be interrogated, e.g., BRCA2. The library is constructed in a cell line for which the loss of the function of the gene to be interrogated is detrimental to cell growth or cell survival. The presence or absence of a variant in the library depends upon the residual function of the allele of the gene to be interrogated after variants are introduced. Relative to a control value, the presence of a threshold fraction of cell lines in the library having an introduced variant in the gene to be interrogated reflects a "benign" function, while the relative or absolute absence of the variant from the library reflects a "deleterious" function. A given cell line in the library may contain many simultaneous variants, permitting the library to be a highly efficient source for the measurements and interpretations accrued into the database.

The invention provides a model in which human gene function could be evaluated based on comparative assessments of the functional impact of individual in-situ sequence alterations of one allele. A syngeneic stable library of sequence variants of BRCA2 exon 27 was constructed. The library enabled the functionally classification of BRCA2 genomic sequence variants of previously unknown significance in a robust manner to help to predict the cancer risk associated with presence of the same mutations in heterozygous patients. Furthermore, the protein based on functional evaluation of subtle protein residue substitutions was investigated.

The SyVaLs of BRCA2 provide a proof of concept of the libraries and methods of the invention for the characterization of mutations in tumor-suppressor genes, or suspected tumor-suppressor genes, or mutations in other genes that result in a loss of function resulting in an increased susceptibility to a specific disease or condition.

First, as a positive control for functional evaluation of SyVaL clones, BRCA2-null cells were generated. Previously, no BRCA2 engineered human gene knock-out cells had been reported. BRCA2 knock-out models exist in mouse, rat, hamster and chicken cells. The pancreatic cancer cell line CAPAN1, the only BRCA2-deficient human cancer cell line, is cumbersome for its low transfectability, poor clonogenicity and lack of isogenic controls. The $BRCA2^{\Delta ex11/\Delta ex11}$ cells disclosed herein provide a stable human cancer syngeneic BRCA2 knock-out model.

The $BRCA2^{\Delta ex11/\Delta ex11}$ cells demonstrated features of BRCA2 deficiency, being defective in homologous recombination as assessed by absence of induction of Rad51 foci upon DNA damage, having chromosomal instability after treatment with mytomycin C (MMC), and being modestly more sensitive to irradiation than syngeneic cells not having the mutation.

To further confirm the BRCA2 phenotype and explore potential treatment options for patients having BRCA2 deficient tumors, an informative panel of drugs was tested in the library of cells. An increased sensitivity to various interstrand cross-linking (ICL) agents and the PARP inhibitor NU1025 was demonstrated, producing pharmacogenetic windows between 10 and 20 (Hucl, T., et al., *Cell Cycle*. 2007. 6, 1336-41).

In the well-controlled human cancer model provided herein, the etoposide hypersensitivity of BRCA2-deficient cells, first reported by Holt and Zdzienicka in CAPAN1 cells and syngeneic hamster cells (Abbott, D. W., et al., *J Natl Cancer Inst*. 1998. 90, 978-85; Wiegant, W. W., et al., *Mutat Res*. 2006. 600, 79-88) was confirmed. Further, it was shown that the difference in sensitivity of the BRCA2 deficient cells to the drug may be even greater (10-fold) than recently reported by Treszezamsky (2.75-fold) in fibroblasts from a Fanconi D1 patient (Treszezamsky, A. D., *Cancer Res*. 2007. 67, 7078-81.). In yeast, the requirement of homologous recombination for topoisomerase-associated toxicity was demonstrated (Hay, T., et al., *Oncogene*. 2005. 24, 3842-6). Not all models have been in agreement. For example, no increased etoposide sensitivity was observed in BRCA2-deficient mouse thymocytes (Flores, K. G., et al., *Mol Carcinog* 2002. 35, 103-9) or small intestines (Walker, J. V., et al., *J Biol Chem*. 2004. 279, 25947-54). The findings thus distinguish cells having defects of the distal (BRCA2, etoposide-hypersensitive) and proximal (no etoposide hypersensitivity) FA pathway (Gallmeier, E., et al., (2006) *Gastroenterology*. 2006. 130, 2145-54). Experiments were extended herein to additional topoisomerase inhibitors. Given the rather low side-effect profile of some of these drugs and the measured pharmacogenetic window of up to 10, data provided herein support their use as candidates for rational treatment of patients with BRCA2-deficient tumors.

The BRCA2$^{\Delta ex11/\Delta ex11}$ cells together with various SyVaL clones thus also represent an optimal model suitable for high-throughput drug screening of compound libraries to identify novel agents having selective toxicity in cells containing pathogenic mutations. No intermediate phenotype of the heterozygous clones was observed, suggesting that use of these drugs may be permissible in cancer patients who are carriers of heterozygous germline BRCA2 mutations.

The lack of understanding of the functional importance and associated cancer risk of sequence variants in the BRCA2 gene represent a serious medical problem. The strongest interpretive evidence tends to come from segregation analyses and observed co-occurrence with known pathogenic mutations, both of which require information that is often not available. Functional studies of human BRCA2 have proven very difficult. Prior cell-based in vitro assays depended upon expression of either partial or complete wild-type or mutant proteins. Testing of partial gene and protein sequences may not fully reveal the influence of the variant on the activity of the intact protein, and findings obtained by their use were not always confirmed using independent types of assay (Goldgar, D. E., et al., *Am J Hum Genet*. 2004. 75, 535-44.). The use of full-length wild-type or mutant constructs has been mostly limited to transient expression since it has proven difficult and at times impossible to generate stably expressing lines. Expression of exogenous BRCA2 including the BRC repeats may result in BRCA2 deficiency, perhaps due to squelching (titrating-out) of free Rad51. Studies utilizing cells having endogenous wild-type BRCA2 alleles depend on the presumption that the co-dominant or dominant-negative effects of exogenous mutated constructs will govern the assay results. Thus, evaluating BRCA2 function utilizing exogenous expression constructs is of extreme technical difficulty.

Provided herein is a new approach to evaluate genomic variants by applying a simple and fast homologous recombination replacement technique to produce syngeneic clones. This syngeneic replacement strategy was approximately as rapid as the stable transfection of routine expression plasmids, a technique with which it shares many invariant steps. Such approach allows an unambiguous read-out by generating multiple clones of stable cell lines having the endogenous gene altered.

A panel of functional assays were applied to a syngeneic knock-out pair and selected two robust assays that in combination provided a clear and unambiguous read-out of BRCA2 function that was applied to a library of variants provided herein: Rad51 focus-formation and MMC sensitivity. By applying these two assays, the positive control was found to have a detrimental phenotype, the negative control to have a neutral phenotype (same as proficient cells), and the two variants of uncertain significance to have a neutral phenotype.

The high ratio, relating the number of clones having integrated a construct into the already targeted allele and the clones having integrated a construct in the wild type allele, observed for the BRCA2$^{\Delta ex11/\Delta ex11}$ cells (80:1) was not observed for any of the exon 27 variants. It is believed that the ratio is influenced by selection against emergence of clones with a detrimental phenotype (Gallmeier, E. et al., *Cancer Biol Ther* 2007. 6:654-60). In addition, the ratio may be potentially influenced by differences in the targeting construct as well as sequence variation or regional differences of chromatin at the targeted locus. This interesting aspect of the technique deserves further investigation.

SyVaLs can also be used to test the function of individual in-situ residues of a protein or regulatory code, unrestricted by the limited number of known natural variants. For such a purpose, the 3291 serine residue of BRCA2, recently evaluated for its phosphorylation, was selected. Cyclin-dependent phosphorylation of this site was shown to inhibit both interaction of BRCA2 with Rad51 and recombination repair. This site was discovered and initially evaluated using expression of partial protein sequences. By mimicking constitutive phosphorylation by substituting serine with glutamate, we observed a hypomorphic phenotype characterized by a decrease in induced Rad51 focus formation and a slight increase in sensitivity to MMC was observed. When serine was replaced with alanine to prevent phosphorylation, neither a decrease in Rad51 focus-formation, nor increased sensitivity to MMC, was observed.

The findings of inhibition of Rad51 focus-formation by the glutamate mutation, and no effect of the alanine mutation, do support the hypothesis of phosphorylation-dependent inhibition of Rad51 interaction. Yet, the use of variant endogenous BRCA2 genes provided a nuanced relation that was not previously determinable. This inhibition was found to be partial, not complete. In addition, where the prior authors saw a surprising inhibitory effect on Rad51 binding also of alanine 3291 when partial peptides were tested, studies herein suggest differently. Phosphorylation of S3291 was found to be dispensable for BRCA2-governed cellular phenotype as judged by the intact function of the alanine 3291 variant, as assayed by a set of robust tests employed herein. The syngeneic lines provided herein thus serve as a staring point in addressing the teleologic purpose, if any, of cell-cycle regulation of the Rad51-BRCA2 interaction.

As demonstrated herein, SyVaLs provide a technically facile, ethically acceptable, means to compare the effects of subtly altering human genomes. Such libraries and methods can be applied to other medically relevant genes, particularly disease associated loss-of-function genes, thus permitting high-throughput annotation of natural human genetic variation. SyVaLs also enable the interrogation of individual codons and regulatory codes in human chromosomes, while avoiding many common artifacts of introducing exogenous genes and gene fragments.

Using methods provided herein, genes associated with Fanconi anemia (FA) were also investigated to detect interaction between different FA genes. Fanconi anemia is a rare, recessively inherited disorder, consisting of congenital skeletal abnormalities, progressive bone marrow failure, and increased cancer risk (D'Andrea A D, and Grompe M. *Nat Rev Cancer* 2003. 3:23-34). The disease comprises at least 12 complementation groups (FANCA, FANCB, FANCC, BRCA2/FANCD2, FANCD2, FANCE, FANCF, FANCG, FANCI, FANCJ, FANCL, and FANCM). All of these genes have been identified except for FANCI (Levitus M, et al., *Blood* 2004; 103:2498-2503; Levitus M, et al.; *Nat Genet*. 2005; Meetei A R, et al., *Nat Genet;* 2005; Meetei A R, et al., *Nat Genet*. 2004. 36:1219-1224).

The FA genes appear to act in a common pathway, distal parts of which interact with regulators of cell cycle control and DNA repair, especially the repair of DNA interstrand crosslinks and double-strand breaks. There are at least three distinguishable compartments of the FA pathway. The upstream element consists of a protein core complex, assembled by FANCA, FANCB, FANCC, FANCE, FANCF, FANCG, FANCL, FANCM, and a yet unidentified 100 kDa protein FAAP100. This complex enables the monoubiquitination of the central protein FANCD2, which subsequently translocates to nuclear DNA repair foci and colocalizes with various DNA repair proteins including BRCA2 (Pichierri P, et al., *Embo J*. 2004. 23:3154-3163; Nakanishi K, et al., *Nat Cell Biol* 2002; 4:913-920; Pichierri P, et al., *Hum Mol Genet*. 2002. 11:2531-2546; Taniguchi T, et al., *Blood* 2002; 100:

2414-2420; Hussain S, et al., *Hum Mol Genet.* 2004. 13:1241-1248; Howlett N G, et al. *Hum Mol Genet.* 2005. 14:693-701; Montes de Oca R, et al., *Blood* 2005; 105:1003-1009; Wang X, et al. *Mol Cell Biol.* 2004. 24:5850-5862). Monoubiquitinated FANCD2 interacts directly with BRCA2 and promotes loading of BRCA2 into chromatin complexes (Wang X, et al., *Mol Cell Biol.* 2004. 24:5850-5862). Whereas defects in any of the proximal FA core proteins preclude FANCD2 monoubiquitination, BRCA2 is not required for this event, supporting that BRCA2 acts downstream of FANCD2. In addition to an intact FA core complex, the checkpoint kinase ATR is also required for FANCD2 monoubiquitination (Andreassen P R, et al. *Genes Dev.* 2004. 18:1958-1963).

Disruption of the proximal FA pathway occurs in different tumor types from non-FA patients, implicating these genes in tumor suppression or genome maintenance among the general population. A subset of pancreatic cancers harbor inactivating mutations of FANCC or FANCG (Couch F J, et al., *Cancer Res.* 2005. 65:383-386; van der Heijden M S, et al., *Am J Pathol.* 2004. 165:651-657; van der Heijden M S, et al., *Cancer Res.* 2003. 63:2585-2588) and FANCF promoter hypermethylation along with gene silencing has been reported in a variety of tumors (Marsit C J, et al., *Oncogene* 2004. 23:1000-1004; Narayan G, et al., *Cancer Res.* 2004. 64:2994-2997; Taniguchi T, et al., *Nat Med.* 2003. 9:568-574). All of these alterations abrogate FANCD2 monoubiquitination.

Disruption of the distal FA pathway also occurs in tumors via mutations in BRCA2. The complete inactivation of BRCA2 function, paradoxically, might predominantly be an adverse event for cancer cells (Van der Heijden M S, et al., *BMC Genet.* 2006; 7:3; Daniels M J, et al., *Science* 2004. 306:876-879). BRCA2 inactivation appears late during tumorigenesis and the mutations almost exclusively yield truncated BRCA2 proteins, which retain partial function (Goggins M, et al., *Am J Pathol.* 2000. 156:1767-1771). In addition, BRCA2 mutations are mainly of germline origin, even in apparently sporadic tumors (Goggins M, et al., *Cancer Res.* 1996. 56:5360-5364; Hahn S A, et al., *J Natl Cancer Inst.* 2003. 95:214-221; Murphy K M, et al. *Cancer Res.* 2002. 62:3789-3793; Ozcelik H, et al., *Nat Genet.* 1997. 16:17-18).

It is demonstrated herein that, similar to complete BRCA2 inactivation, the complete inactivation of FANCD2, but not the mere reduction of FANCD2 protein levels, was detrimental in an experimental human cancer model. It was further confirmed that human cancer cells that harbor the "Seckel" ATR mutation display defective FANCD2 monoubiquitination, FANCD2 nuclear focus formation and increased sensitivity to DNA interstrand-crosslinking agents. Nevertheless, these ATR Seckel cells were viable, suggesting that the detrimental phenotype in human cancer cells upon complete FANCD2 inactivation in our model is not readily attributable to the major known functions of FANCD2.

Using somatic cell gene targeting, both alleles of several FA genes were sequentially targeted at different levels of the FA pathway. In contrast to the complete disruption of FANCC and FANCG, it was not possible to disrupt both alleles of BRCA2 or FANCD2. The BRCA2 gene differs from other FA genes in that it serves essential functions, which might be either related to or independent from the FA pathway (Venkitaraman A R. *Nat Rev Cancer* 2004. 4:266-276). BRCA2 exhibits a high degree of conservation within the BRC-repeat regions (Sharan S K, and Bradley A. *Genomics* 1997. 40:234-241), whereas the proximal FA genes are not well conserved. Consistently, knockout mice having null mutations of BRCA2 are embryonic lethal. Only truncating mutations in BRCA2 that spare some of the BRC repeats can confer a viable phenotype (Bennett L M, et al. *Mol Carcinog.* 2000. 28:174-183; Connor F, et al., *Nat Genet.* 1997. 17:423-430; Friedman L S, et al., *Cancer Res.* 1998. 58:1338-1343; Ludwig T, et al., *Genes Dev.* 1997. 11:1226-1241; McAllister K A, et al., *Cancer Res.* 2002. 62:990-994; Sharan S K, et al., *Nature* 1997. 386:804-810; Suzuki A, et al., *Genes Dev.* 1997. 11:1242-1252). FANCA, FANCC, and FANCG knockout mice display normal viability and do not display gross growth abnormalities (Chen M, et al., *Nat Genet.* 1996. 12:448-451; Cheng N C, et al., *Hum Mol Genet.* 2000. 9:1805-1811; Koomen M, et al., *Hum Mol Genet.* 2002. 11:273-281; Whitney M A, et al., *Blood* 1996. 88:49-58; Wong J C, et al., *Hum Mol Genet.* 2003. 12:2063-2076; Yang Y, et al., *Blood* 2001. 98:3435-3440). Similarly, the complete disruption of BRCA2 is a lethal event in chicken DT40 cells (Warren M, et al., *Hum Mol Genet.* 2003; 12:2645-2656), whereas the introduction of truncating BRCA2 mutations that spared two BRC repeats, only decreased the growth rate in these cells (Hatanaka A, et al., *Mol Cell Biol.* 2005. 25:1124-1134). Disruption of FANCC (Hirano S, et al., *Embo J.* 2005. 24:418-427; Niedzwiedz W, et al., *Mol Cell* 2004. 15:607-620) or FANCG (Yamamoto K, et al., *Mol Cell Biol.* 2003. 23:5421-5430) did not impair cell viability in DT40 cells. Therefore, the results provided herein are consistent with the hypothesis that the complete inactivation of BRCA2 function might predominantly be an adverse event for cancer cells.

In contrast, the data provided herein suggest that FANCD2 inactivation was selected against in cancer cells were rather unexpected and two different cancer cell lines were employed to rule out cell line-specific artifacts. No significant differences were found between FANCD2 protein-depleted and control cells in regard to cell death, proliferation, or cell cycle profile, and additionally, observed no functional haploinsufficiency in FANCD2$^{+/-}$ clones, the remaining FANCD2 protein was likely sufficient to prevent any detrimental phenotype dependent upon a complete FANCD2 loss. A similar phenomenon can be observed in cancer cells having impairment of the FA pathway-related gene ATR, which is required for the major known functions of FANCD2 (Andreassen P R, et al., *Genes Dev.* 2004; 18:1958-1963) complete ATR gene disruption is a lethal event (Cortez D, et al., *Science* 2001. 294:1713-1716), whereas subtotal ATR protein depletion has no gross effects on cellular viability (Hurley et al., *Oncogene* 2007. 26:2535-42. Epub 2006 Oct. 16). Using ATR$^{s/s}$ cancer cells, it was demonstrated herein that the DNA damage-induced FANCD2 monoubiquitination and nuclear focus formation, representing the best-characterized functions of FANCD2 (Gregory R C, et al., *Semin Cancer Biol.* 2003. 13:77-82), are both ATR-dependent (Andreassen P R, et al. *Genes Dev.* 2004. 18:1958-1963). Maybe surprisingly, by using p53-mutant cells, it was demonstrated herein that these ATR/FA pathway interactions are p53-independent. ATR$^{s/s}$ cancer cells displayed a quantitatively comparable MMC hypersensitivity as did FANCC$^{-/-/-}$ and FANCG$^{-/-}$ cancer cells (Gallmeier E, et al., *Gastroenterology* 2006; 130:2145-2154), indicating a similar role for ATR, FANCC and FANCG in FA pathway-mediated DNA repair, and further supporting that ATR acts upstream of FANCD2. However, as disruption of FANCC or FANCG also impairs FANCD2 focus formation and completely abrogates FANCD2 monoubiquitination, the loss of ATR-dependent FANCD2 functions alone cannot account for the observed selection against FANCD2 inactivation in our model. These studies demonstrate the utility of the methods of the invention to classify the interaction of multiple potential loss-of-function mutations in a single cell.

The proposition put forth herein that FANCD2 inactivation is predominantly selected against in cancer cells is supported by considerable evidence that the FANCD2 gene, like the BRCA2 gene, might be essential; FANCD2 is highly conserved (Timmers C, et al., *Mol Cell* 2001. 7:241-248), and some FANCD2 knockout mice, depending on the background strain, exhibit perinatal lethality, suggesting the presence of a modifier locus (Houghtaling S, et al., *Genes Dev.* 2003. 17:2021-2035). Furthermore, developing tissues spontaneously undergo apoptosis in the absence of FANCD2, as shown in a zebrafish model (Liu T X, *Dev Cell* 2003. 5:903-914). The hypothesis is also not inconsistent with the existence of patients harboring biallelic FANCD2 mutations, as all of these patients reported to date have at least one mutant allele that could have some residual function (Houghtaling S, et al., *Genes Dev* 2003, 17:2021-2035). Consistently, lymphocytes from some FA patients of the complementation group FANCD2 contain FANCD2 protein. Another explanation would suggest that normal cells might be able to sustain inactivation of FANCD2, in contrast to certain cancer cells, which could be ascribed to defective checkpoints in cancer cells, a deleterious increase in mutation rate, or additional defects in DNA repair genes apart from FANCD2.

On the other hand, FANCD2 gene defects are obviously not always detrimental to cancer cells, as FA patients of the complementation group FANCD2 and FANCD2 knockout mice do indeed get cancers. This could be explained by the mutational profile of a cancer representing the balance of selective pressures for and against any given mutation, with the likely possibility that both directions of selection operate on even single genes. Consequently, cancer cells having naturally selected for a FANCD2 defect may differ significantly from cells on which this gene defect was experimentally superimposed, due to the mutually dependent effects of reduction of fitness and compensatory evolution that might occur upon or even prior to FANCD2 disruption. Cells having naturally selected for a FANCD2 defect already would have evolved, as a precondition, a compensatory genotype. In contrast, when this gene defect was superimposed in an experimental setting, cells would have little opportunity for compensation.

In summary, study herein illustrates the distinct impact of experimental gene disruption of FA genes at different stages of the FA pathway on human cancer cells providing a synthetic lethal type screen. The distal FA genes BRCA2 and FANCD2, in contrast to the proximal FA genes, appear to represent particularly vulnerable parts of this pathway. The extent of reduction of fitness induced by their inactivation may, under most circumstances, override the potentially gained advantage of FA pathway inactivation in tumors. This could explain why certain FA gene defects, despite an apparent selection for FA pathway inactivation in cancer, are rarely observed in tumors among the general population.

It is demonstrated herein that in human cancer cells the experimental gene disruption of the FA genes FANCC and FANCG, which act upstream in the FA pathway, are well tolerated, whereas the disruption of FANCD2 and BRCA2, which act downstream, is detrimental. It is further demonstrated that, similar to BRCA2 inactivation, selection against FANCD2 inactivation is dependent on a complete FANCD2 loss. Finally, the detrimental phenotype of cancer cells having FANCD2 inactivation is not attributable to the major known, ATR-dependent functions of FANCD2. This study establishes that the downstream FA genes FANCD2 and BRCA2 represent particularly vulnerable parts of the FA pathway in cancer cells and provides direct evidence for the paradoxical assumption that their inactivation, despite an apparent selection for FA pathway inactivation in many tumors, could be predominantly selected against in cancer cells.

The libraries and methods provided herein allow for the analysis of the function of various tumor-suppressor genes, allowing for the selection and/or identification of appropriate chemotherapeutic agents for the prevention or treatment of cancer. For example, if a tumor-suppressor gene with an unknown function results in a synthetic lethal phenotype when combined with a tumor-suppressor gene of a known function, e.g., DNA repair, cell cycle regulation, transcriptional regulation, cellular transport, it is likely that the tumor-suppressor gene of unknown function has a role in the same pathway as the tumor-suppressor gene of known function.

Identification of a role for a tumor-suppressor gene can facilitate the rational selection of chemotherapeutic or chemopreventive agents for the treatment or prevention of cancer. As demonstrated herein, cells including a BRCA2 mutation are more susceptible to double-strand breaks, suggesting the use of specific types of agents. The syngeneic variance libraries of cells of the invention can be tested for their sensitivity to various agents. The cells of the variance libraries can be transformed with various mutations observed in a population, or in a specific patient, to determine what agents may be most effective at treating or preventing disease.

Test Compounds and Extracts

In general, agents with desired biological or pharmacological properties are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include those known as therapeutics or approved for use in humans. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries can include collections of known chemical agents, for example, agents approved for administration to humans.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have the desired activity, further fractionation of the positive lead extract is necessary to isolate molecular constituents responsible for the observed effect. Thus, the goal of the extraction, fractionation, and purification process is the careful characterization and identification of a chemical entity within the crude extract that is useful as a therapeutic. Methods of fractionation and purification of such heterogenous extracts are known in the art. If desired, compounds shown to be useful as therapeutics are chemically modified according to methods known in the art.

Kits

The invention provides kits for the practice of the methods of the invention. Kits can include one or more cell lines of the invention, e.g., a library of syngeneic variant cells, and instructions for use in appropriate packaging. The library can further be packaged with both positive and negative control fragments for use with the cell lines.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991); Antibody Phage Display, (O'Brien and Aitken, 2002). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

This invention is further illustrated by the following examples, which should not be construed as limiting.

Examples

Example 1

Materials and Methods

Cell Lines and Cell Culture

DLD1 cells were obtained from ATCC, cultured in conventional media supplemented with 10% fetal calf serum, L-glutamine and penicillin/streptomycin.

Targeted Disruption by Homologous Recombination

Exon 11 of BRCA2 was disrupted by homologous recombination using the technique of Kohli et al. (*Nucleic Acids Res.* 2004. 32, e3, incorporated herein by reference). The targeting construct was designed to excise a part of exon 11, containing a known mutation and including BRC repeat 6, thus causing a premature stop codon after BRC repeat 5. Hygromycin-resistant clones having homologous integration of targeting construct were identified by PCR, using a primer inside the resistance gene and a primer outside of the homology arms (SEQ ID NOs 36039) using known methods. The selection cassette was removed by transiently expressing exogenous Cre recombinase. A recombinant hemizygous clone, indentified by PCR using primers flanking the deletion, was used for second allele targeting. Reusing the same exon 11 targeting construct, clones acquiring biallelic disruption of BRCA2 were identified by PCR screening using a combination of primers described above.

Alternately, exon 27 was targeted in the hemizygous cells using a construct whose right homology arm included intact exon 27 and individual sequence variants. Homologous integration of the construct, the presence of desired sequence variants and allelic phase of the construct were determined by allele-specific PCR and sequencing. An analogous vector design was used by Hurley et al. to introduce an ATR mutation into alleles of a human cell (Hurley, P. J. et al., *Oncogene.* 2007. 26, 2535-42, incorporated herein by reference).

DNA, RNA Isolation, PCR, Sequencing

Genomic DNA was isolated from cells using Lyse-N-Go® (Pierce). RNA was isolated using RNeasy® Mini Kit (Qiagen, Valencia, Calif.). Automated sequencing was performed by a core facility. PCR conditions and primer sequences are available upon request.

Allele-Specific PCR

The presence of the targeting construct and its subsequent cre-mediated removal enabled selective amplification from one of two alleles using primers specific for either the construct or the deleted sequence.

Digital PCR

Digital PCR was performed essentially as described previously (Vogelstein, B. & Kinzler, K. W. *Proc Natl Acad Sci*

USA 1999. 96, 9236-41, incorporated herein by reference). In a duplex reaction, primers specific for deletion-specific sequences at exon 11 and spanning intron 25 were combined.

Site-Directed Mutagenesis

Mutated targeting constructs were generated using the QuickChange Site-Directed Mutagenesis Kit (Stratagene, LaJolla, Calif.).

Northern Blotting

For northern blotting, random primer-labeled cDNA was used to detect BRCA2 exon 11 mRNA, and end-labeled oligomers were used to detect 18S rRNA (Lal, A., et al. *Embo J.* 2004. 23, 3092-102.).

Cell-Cycle Analysis

Cells were treated with MMC for 48 hours, processed as described previously (Vindelov, L. L., et al., *Cytometry* 1983. 3: 323-7, incorporated herein by reference) and analyzed by flow cytometry.

Chromosome Aberration Assay

Cells were treated with equitoxic doses of MMC (80 nM for BRCA2$^{wt/\Delta ex11}$ and 6 nM for BRCA2$^{\Delta ex11/\Delta ex11}$) for 24 h. For each sample, 50 metaphases were analyzed using standard techniques by a core facility.

Cell Proliferation Assay

In each well of 96-well plates, 1000 cells were plated, allowed to adhere and treated with various drugs. The drugs were obtained from Sigma (St. Louis, Mo.) except for SJG-136 which was generously provided by Ipsen Ltd. and the National Cancer Institute, NIH. The cells were washed after 6 days and lysed in 100 uL of water. Fluorescence was measured after addition of 0.5% Picogreen® (Molecular Probes, Eugene, Oreg.) using a fluorometer (Fusion®, Perkin Elmer, Shelton, Conn.). Three independent experiments were performed per drug.

Colony-Formation Assay

Cells were plated in 6-well plates, allowed to adhere and exposed to $^{137}$Cs gamma rays. After 14 days, cells were washed and stained with crystal violet and colonies were counted. For each dose, cells were plated at 3 different concentrations in duplicate. Three independent experiments were performed.

Immunofluorescence

Cells were treated with MMC (2.4 µg/ml) or gamma irradiation and fixed in PBS/2% paraformaldehyde after 24 h incubation. Following permeabilization in PBS/0.5% Triton X-100 and blocking for 30 min in PBS/1% bovine serum albumin/0.15% glycine, the cells were incubated with an anti-Rad51 antibody (1:200, Calbiochem, San Diego, Calif.) for 2 h. Cells were then washed and incubated with a rabbit IgG secondary antibody (1:200, Alexa® 488, Molecular Probes, Eugene, Oreg.) for 1 h. After washing, slides were mounted and analyzed by a fluorescent microscope (Zeiss Axiover 135, Maple Grove, Minn.) and Metamorph 4.6 software (Universtal Imaging, Downington, Pa.). Pictures were acquired, keeping exposure time and software settings constant for all samples.

Baseline or induced Rad51 focus formation was considered "negative" when less than 5% or 20%, respectively, of cells had more than 5 nuclear foci and "positive" when more than 5% or 30%, respectively, of cells had more than 5 nuclear foci. Intermediate phenotypes were not observed.

Somatic Cell Gene Targeting

Figure 3:
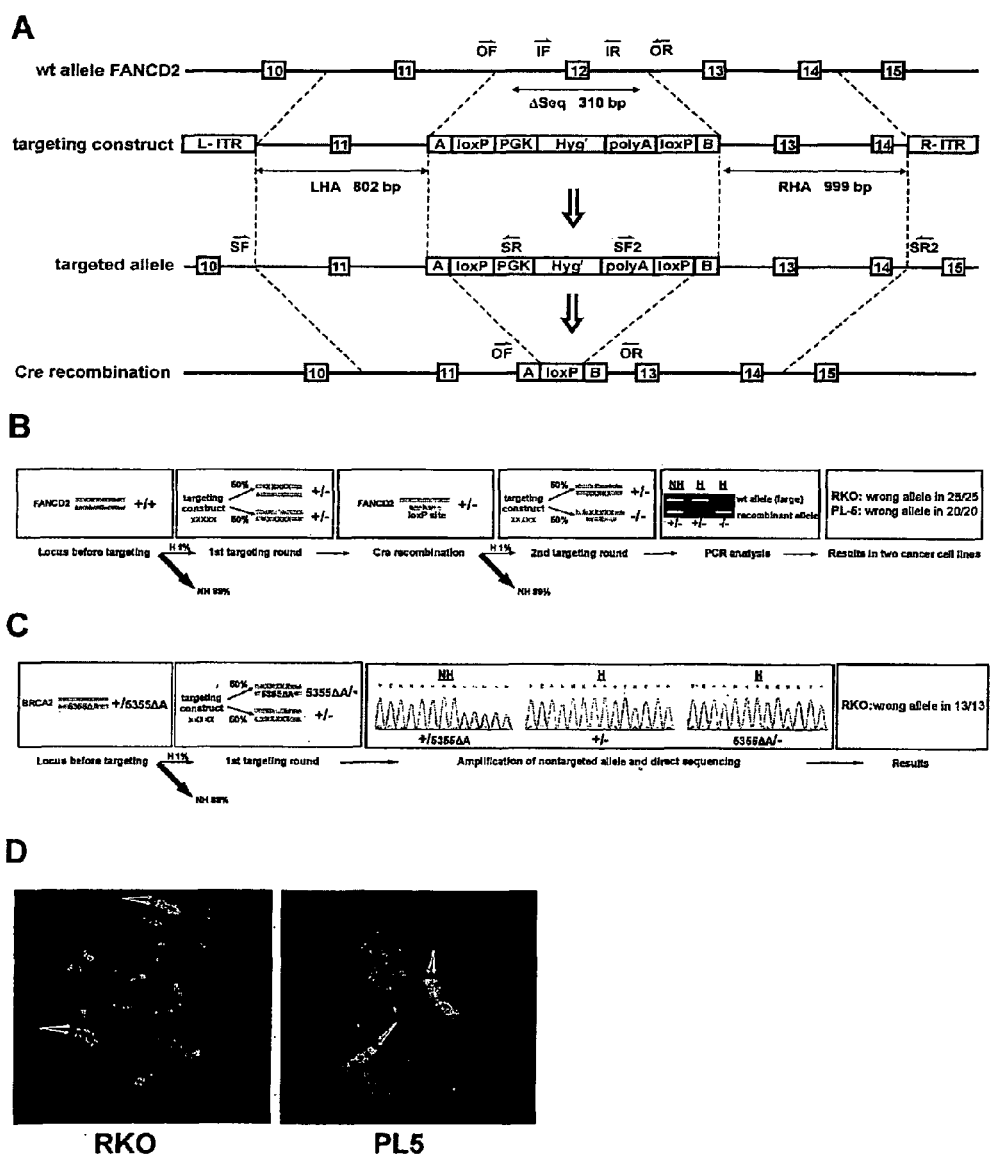
FIG. 3. Gene targeting of FANCD2 and BRCA2 and confirmation of diploidy. (A) Schematic targeting procedure. OF+OR primer set outside and IF-FIR primer set inside the deleted sequence; SF+SR and SF2+SR2 screening primer sets; LHA+RHA left and right homology arms. (B) Schematic representation of targeted allele determination for FANCD2. The integration of the targeting construct (xxxxx) at the FANCD2 locus would result in a very large PCR product when using the primers OF+OR, which would not be amplified unless the construct is removed using Cre recombination (x). Note that most of the resultant clones of a given targeting round represent non-homologous integration (NH) of the targeting construct (~99%). Homologous integration (H) of the construct is presumed to randomly target either FANCD2 allele with a 50% probability. (C) Schematic representation of targeted allele determination for BRCA2. Following one round of gene targeting, direct sequencing of the region surrounding the 5535AA mutation was performed to identify whether the wild-type or the mutant allele was targeted and to distinguish clones having nonhomologous integration from clones having homologous integration of the construct. (D) Whole-chromosome painting of chromosome 3 (red) and FISH analysis, using a FANCD2-specific probe (yellow), confirmed diploidy at the FANCD2 locus in RKO and PL5. Arrows indicate FANCD2-specific probes. Note that the unbalanced translocation of chromosome 3 material to another chromosome in RKO cells does not show a signal from the FANCD2-specific probe.

The endogenous FANCC, FANCG, FANCD2, and BRCA2 genes were disrupted in somatic cells according to a recently developed technique (Kohli M, 2004; Gallmeier E, 2006). The targeting constructs of FANCC, FANCG, and FANCD2 were designed to replace one exon, in each case causing a premature stop codon (Table 2). The targeting constructs were ligated into pAAV-MCS (Stratagene, La Jolla, Calif.) and co-transfected with pAAV-RC and pHelper into colorectal adenocarcinoma RKO and pancreatic adenocarcinoma PL5 cells. Hygromycin-resistant clones were selected and clones having homologous integration of the targeting construct identified by PCR, using one primer inside the resistance gene and one outside of the left or right homology arm, respectively (SF/SR and SF2/SR2). The selection cassette was subsequently removed using Cre recombinase. Recombinant clones, identified by PCR using primer sets inside (IF-HR) and outside (OF-FOR) of the selection cassette, were used to sequentially target the second allele (FIG. 3A). Finally, PCR using primers flanking the targeting construct identified which of the alleles had been targeted in the second targeting round. The absence of a product from the wild-type allele would confirm homozygously targeted clones (FIG. 3B).

BRCA2 gene disruption was performed similarly, but with the following modifications. RKO cells contain a heterozygous frameshift mutation in exon 11 of the BRCA2 gene (BRCA2$^{wt/5355\Delta A}$), allowing the disruption of BRCA2 function through only one round of gene targeting. The targeting construct was designed to replace the distal part of exon 11, causing a premature stop codon after BRC repeat 5, predicted to severely impair BRCA2 function. Clones having homologous integration events were identified by PCR. Subsequently, the nontargeted allele was specifically amplified and sequenced. The presence of the 5355AA mutation in a homozygous state would identify clones harboring a functional disruption of the BRCA2 gene (BRCA2$^{5355A\Delta/-}$) (FIG. 3C).

siRNA-Mediated Knockdown of FANCD2

Cells at about 70% confluency were transfected with three different FANCD2 short interfering RNAs (siRNA) (Ambion, Austin, Tex.) or scrambled siRNA, at final siRNA concentrations of 25 nM, using Oligofectamine® (Invitrogen, Carlsbad, Calif.). Transfection proceeded for four hours before adding serum-containing medium. FANCD2 protein depletion was quantified by immunoblotting 48 h after transfection.

Immunoblotting

Protein lysates from 200,000 cells were separated on 3-8% tris-acetate gels for 165 min at 150V, and transferred to PVDF membranes. After blocking, the membranes were incubated overnight with monoclonal mouse anti-human FANCD2 or polyclonal goat anti-human ATR antibodies (both 1:1000, both Santa Cruz, Santa Cruz, Calif.). Membranes were then washed and probed with the corresponding secondary antibody (1:10,000, Pierce, Rockford, Ill.). Detection was performed using the SuperSignal West Pico Substrate (Pierce). Equal protein loading was verified by membrane staining of total protein with Fast Green® (USB, Cleveland, Ohio).

Immunofluorescence

Cells at about 70% confluency were treated with mitomycin C (MMC) at 100 nM for 24 h, fixed in PBS/4% paraformaldehyde, washed, and fixed in −20° C. methanol. Following permeabilization in TBS/0.5% Triton X-100 and blocking for 30 min in TBS/2% bovine serum albumin/0.5% Triton X-100, the cells were incubated with a monoclonal mouse anti-human FANCD2 antibody (1:200, Santa Cruz) for 2.5 h. Cells were then washed and incubated with a goat anti-mouse IgG secondary antibody (Alexa® 488, Molecular Probes, Eugene, Oreg.) for 1.5 h. After washing, slides were mounted and analyzed. Pictures were acquired keeping exposure time and software settings constant for all samples.

Cell Proliferation Assays

For siRNA experiments, the cells were plated in 6-well plates at 500,000 cells/well at 24 h after siRNA transfection. Separate aliquots of each sample were counted at six different time points one to four days after transfection, using two separate aliquots for each time point. Dead cells were separately determined by trypan-blue exclusion and were negligible in number in all samples (<2%). For comparisons between parental cells and FANCD2$^{+/-}$ clones, 500,000 cells/well were plated and counted at six time points between 0 and 48 h. Two independent experiments were performed. For MMC sensitivity studies, Picogreen® (Invitrogen) proliferation assays were performed in quadruplicate as described in Gallmeier et al., 2006.

Cell Cycle Analysis

Cells were detached, washed, and fixed in PBS/3.7% formaldehyde/0.5% Nonidet P40 (USB). Nuclei were stained with bisbenzimide (Hoechst 33258, Sigma, St. Louis, Mo.) and analyzed by flow cytometry. 10,000 events were acquired per sample. The data were processed using Cell Quest® software (Becton Dickinson).

Allele-Specific PCR and Direct Sequencing

Genomic DNA was prepared from cells using either the DNA Blood Mini kit (Qiagen, Valencia, Calif.) or Lyse-N-Go® (Pierce). PCR was performed using 38 cycles with differing annealing times for each primer set. The products were resolved on 0.7% agarose gels using tris-free electrophoresis (Faster Better Media LLC, Hunt Valley, Md.). The introduction of the targeting construct in one allele allowed the specific amplification of the non-targeted allele using primers outside the homology arms on either side, which, due to fragment size, did not yield a product from the targeted allele. Automated sequencing was performed by the Biosynthesis and Sequencing Core Facility at Johns Hopkins using routine methods.

Whole-Chromosome Painting and Fluorescence In-Situ Hybridization (FISH)

Whole-chromosome 3 painting and FISH analysis, using the BAC clone RP11-1016H17 (CHORI, Oakland, Calif.), were performed by the Cytogenetics Core Facility at Johns Hopkins using routine methods.

Example 2

Targeted Disruption of BRCA2

Initial attempts to disrupt the remaining wild-type allele in a BRCA2 heterozygous, p53-wild-type cell line RKO (BRCA2$^{wt/5355delA}$), but viable BRCA2-null clones could not be obtained.

Subsequent attempts used the diploid p53-deficient cancer cell line, DLD1. DLD1 cells originally harbored two nonsense mutations of BRCA2. Both mutations are present on one allele. In the first round of BRCA2 targeting, exon 11 of this allele was deleted, ensuring a permanent null state without a possibility of the mutations' reversion. The other allele in the hemizygous clone remained wild-type.

In the second round of BRCA2 targeting, 81 viable clones having homologous integration of the targeting construct were obtained in several independent targeting attempts, of which only 1 clone had integrated the construct in the wild-type allele, producing a homozygous BRCA2$^{\Delta ex11/\Delta ex11}$ knockout. The other 80 clones had re-integrated the construct into the already-knockout out allele.

PCR and northern blot analyses confirmed the heterozygous and homozygous gene disruption. Northern blot revealed the expression of exon 11 transcript in the parental and heterozygous populations. There was no detectable transcript in the homozygous cells.

Example 3

Functional Analysis of BRCA2$^{\Delta ex11/\Delta ex11}$ Cells

Both engineered and natural cells harboring truncated BRCA2 exhibit a proliferative impediment that may worsen with successive passages. The proliferation rate and doubling time in the BRCA2$^{\Delta ex11/\Delta ex11}$ cells generated herein was found to be slower than syngeneic controls, as determined by direct cell counting and by assaying DNA content of the culture. The proliferation rates of the cells corresponded to the following doubling times: BRCA2$^{wt/wt}$ 0.92±0.14, BRCA2$^{wt/\Delta ex11}$ 1.00±0.3, BRCA2$^{\Delta ex11/\Delta ex11}$ 1.47±0.13 days (SEM). This slight proliferation defect appeared stable with successive passage in culture.

Example 4

Rad51 Focus-Formation

Figure 2:
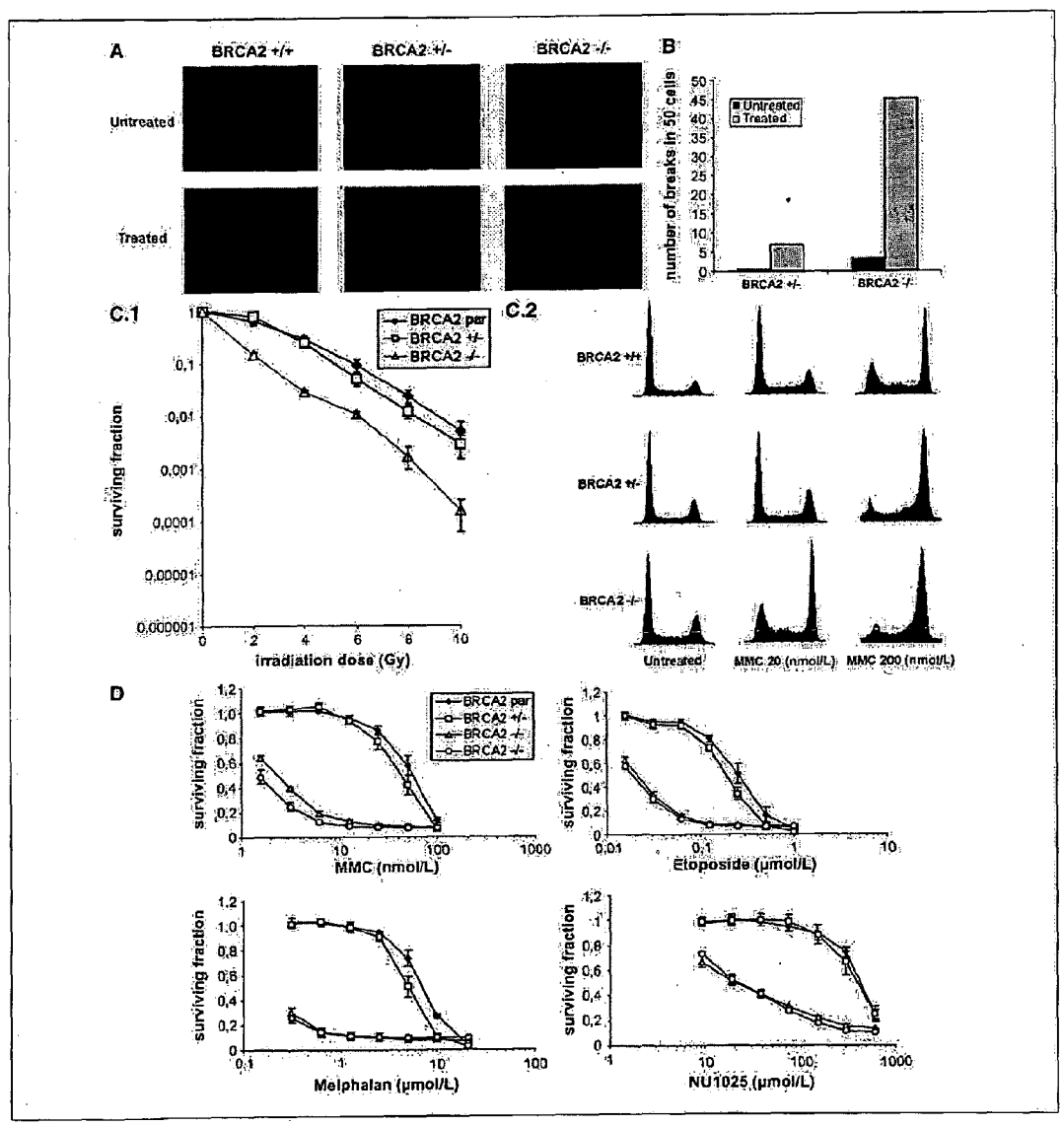
FIG. 2. Characterization of BRCA2-null cells. (A) Immunofluorescence of Rad51 nuclear foci in untreated and treated cells (2.4 mg/ml MMC). $BRCA2^{+/-}$, $BRCA2^{wt/\Delta ex11}$; $BRCA2^{-/-}$, $BRCA2^{\Delta ex11/\Delta ex11}$. (B) Analysis of 50 metaphase chromosomeal aberrations in untreated and treated equitoxic doses of MMC heterozygous and knockout clones. (C.1) Colony formation assays upon irradiation. BRCA2 par, parental $BRCA2^{wt/mut \times 2}$. Points, mean of three independent experiments; Bars SE. (C.2) Cell cycle analysis 48 h after MMC treatment. Representative cell cycle profiles obtained after treatment with indicated concentrations of MMC. Error bars represent SEM of 3 independent experiments. (D) Cell proliferation following treatment with selected drugs. Two $BRCA2^{-/-}$ ($BRCA2^{\Delta ex11/\Delta ex11}$) subclones were analyzed. Error bars represent SEM of 3 independent experiments.

To investigate whether the BRCA2$^{\Delta ex11/\Delta ex11}$ cells were defective in homologous recombination, their ability to form Rad51 foci upon DNA-damage induction was examined. Treatment with MMC induced Rad51 foci (more than 5 foci) in about 60-80% of BRCA2 proficient cells, and with irradiation, in about 50-60% of cells. BRCA2$^{\Delta ex11/\Delta ex11}$ cells had reduced levels of foci in untreated cells, and no induction of foci was observed upon DNA damage (FIG. 2A).

Example 5

Chromosomal Instability

BRCA2-deficient cells display increased chromosomal instability, which was further enhanced after treatment with MMC. Treatment-induced breakage serves as a diagnostic test for the FA syndrome, including the FA-D1/BRCA2 group. BRCA2$^{\Delta ex11/\Delta ex11}$ displayed much higher rates of chromosomal aberrations than BRCA2$^{wt/\Delta ex11}$ cells, including breaks and radials, upon MMC treatment at equitoxic doses (FIG. 2B).

Cell survival after irradiation. There has been conflicting data regarding the sensitivity of BRCA2-deficient cells to irradiation. Therefore, the impact of BRCA2 disruption on survival was assessed after treatment with X-rays. A decrease by half in relative survival of BRCA2$^{\Delta ex11/\Delta ex11}$ cells compared to their controls was observed (FIG. 2B).

Example 6

Cell Proliferation Upon Drug Treatment

The role of BRCA2 in DNA repair and replication fork maintenance is indicated by the hypersensitivity of BRCA2-defective cells to DNA-damaging agents. Survival following exposure to several clinically relevant drugs in parental cells, heterozygous and homozygously deleted cells was assayed.

BRCA2-deficient cells exhibited greatly increased sensitivity to various interstrand-crosslinking (ICL) agents, including MMC, melphalan, cisplatin, carboplatin, SJG and oxaliplatin (FIG. 2D).

Topoisomerase inhibitors affect enzymes incising either one (topoisomerase I inhibitors) or two (topoisomerase II inhibitors) strands of DNA in the process of DNA replication. The BRCA2-deficient cells described herein displayed increased sensitivity to topoisomerase II inhibitors etoposide (10-fold) and doxorubicin (10-fold), and to a smaller extent topoisomerase I inhibitor camptothecin (6-fold) (FIG. 2D). Etoposide hypersensitivity was additive to, but not synergistic with, other anticancer agents.

Hypersensitivity of BRCA2-deficient cells to PARP inhibitors has been reported. The cells described herein having an acute disruption of BRCA2 were more sensitive (20-fold) to NU1025 than control cells (FIG. 2D).

No differences in sensitivities to gemcitabine and vinblastine as well as to agents that have various DNA damaging potential, such as norethindrone, apigenin, curcumin and hesperidin were observed.

(10067C→A, P3280H; 10103C→T, P3292L) listed in the BRCA2 mutation database (http://research.nhgri.nih.gov/bic/) as variants of uncertain significance were examined (Table 1).

TABLE 1

Characterization and proposed classification of BRCA2 SyVaL clones.

| Clone | Rad51 | MMC | Etoposide | Chromosome Instability | Classification |
|---|---|---|---|---|---|
| BRCA2$^{wt/\Delta ex11}$ | Pos | NoΔ | NoΔ | Neg | Neutral |
| BRCA2$^{\Delta ex11/\Delta ex11}$ | Neg | 20-foldΔ | 10-foldΔ | Pos | Deleterious* |
| BRCA2$^{\Delta ex11/Y3308X}$ | Neg | 20-foldΔ | 10-foldΔ | — | Deleterious |
| BRCA2$^{\Delta ex11/Y3308Y}$ | Pos | NoΔ | NoΔ | — | Neutral |
| BRCA2$^{\Delta ex11/P3292L}$ | Pos | NoΔ | NoΔ | — | Neutral |
| BRCA2$^{\Delta ex11/P3280H}$ | Pos | NoΔ | NoΔ | — | Neutral |
| BRCA2$^{\Delta ex11/S3291E}$ | Neg | 3-foldΔ | 3-foldΔ | — | Hypomorphic |
| BRCA2$^{\Delta ex11/S3291A}$ | Pos | NoΔ | NoΔ | — | Neutral |

Pos, positive.
Neg, negative.
Δ, change.
FoldΔ refers to the ratio of the IC50 of cells having the hemizygous wild-type allele to the IC50 of cells having the mutated allele.
—, not done.
*The extreme rarity of knock-out clones may indicate an especially severe deleterious effect.

The increased genotype-dependent toxicity to MMC was confirmed by flow cytometry, indicating a profound G2/M arrest of the cell cycle.

Example 7

Distinguishing Homologous Recombination Events Affecting the Active or Inactive Allele ("Phase" Determination)

The hemizygous BRCA2$^{wt/\Delta ex11}$ cells, having one active and one inactive allele, were used for subsequent experiments. In preparation to target exon 27, residing at a large genomic distance from exon 11, a method was devised to readily distinguish long-distance cis relations of each allele. First automated sequencing of the heterozygous cell line was performed to identify natural, pre-existing heterozygous nucleotide polymorphisms within intron 25. Next analysis was performed to distinguish whether the intronic polymorphisms were on the active or inactive allele (termed the "phase") by determining whether they were in cis or in trans to the deleted exon, using limiting dilution of the template DNA and digital duplex PCR (Couch F J, et al., Cancer Res. 2005. 65:383-386, incorporated herein by reference). Primers were specific for the exon 11 deletion sequence or flanked the identified polymorphisms. Sequencing was performed to identify the allele amplified in each well.

Example 8

Introducing Sequence Variants into Exon 27

The heterozygous clone used for exon 27 targeting was verified to have intact BRCA2 function by demonstrating an absence of mitomycin hypersensitivity and the formation of Rad51 foci upon DNA damage (FIG. 2A, D). A series of mutations was introduced by site mutagenesis into a targeting construct whose original right homology arm included wild-type exon 27 (Table 1). As a positive control, a known deleterious nonsense mutation, (10152C→G, Y3308X) was used. As a negative control, a synonymous mutation was introduced in the same codon (10152C→T, Y3308Y). Two naturally occurring missense human sequence variants Example 9

Analysis of Importance of Phosphorylation of BRCA2 at S3291

The significance of the recently reported phosphorylation site in exon 27, S3291 was investigated by introducing a glutamate (mimicking constitutive phosphorylation of the protein) and alanine (to prevent phosphorylation) at codon 3291.

On average for each mutation, 20 clones having homologously integrated the targeting construct were identified by PCR; between 30 to 80% of these clones harbored the introduced mutation. The phase of the construct was subsequently determined in these clones by PCR and sequencing. Clones having integrated the mutated construct into the inactive allele, as well as clones having integrated the targeting construct at an unrelated genomic site, were used as controls in the functional assays.

Example 10

Functional Evaluation of SyVaL Clones

The robust and reproducible differences between wild-type BRCA2$^{wt/wt}$ and BRCA2$^{\Delta ex11/\Delta ex11}$ cells in drug treatment assays and in Rad51 focus-formation assays (Table 1 and FIG. 1) suggested that these tests were well suited to evaluate the impact of introduced mutations on BRCA2 function.

Example 11

MMC and Etoposide Sensitivity

BRCA2$^{\Delta ex11/Y3308X}$ had profound sensitivity to MMC and etoposide (20 and 10-fold, respectively), whereas BRCA2$^{\Delta ex11/Y3308Y}$ did not differ from control cells. BRCA2$^{\Delta ex11/P3280H}$ and BRCA2$^{\Delta ex11/P3292L}$ were not significantly more sensitive than the corresponding controls. BRCA2Δex11/S3291E, but not BRCA2$^{\Delta ex11/S3291A}$, were 3-fold more sensitive than controls (Table 1).

Example 12

Rad51 Focus-Formation

Rad51 focus-formation was drastically diminished in untreated and treated BRCA2$^{\Delta ex11/Y3308X}$ (a negative assay result), but robust in BRCA2$^{\Delta ex11/Y3308Y}$ cells (a positive, normal result). No significant reduction in focus-formation was observed in BRCA2$^{\Delta ex11/P3280H}$ and BRCA2$^{\Delta ex11/P3292L}$ (each, positive). A significant decrease in focus-formation upon MMC treatment was in BRCA2$^{\Delta ex11/S3291E}$ (negative), but not BRCA2$^{\Delta ex11/S3291A}$ cells (positive) (Table 1).

Example 13

Gene Targeting of FANCD2

The first allele of the FANCD2 gene was disrupted in human adenocarcinoma cells (RKO) by deleting exon 12, predicted to produce a premature stop codon 51 by downstream of the exon 11/13 junction (Table 2 and FIG. 3A). Five FANCD2$^{+/-}$ clones were obtained.

Targeting of the second allele in FANCD2$^{+/-}$ clones did not yield FANCD2 clones having inactivation of both alleles. Instead, 25 clones had reintegrated the targeting construct into the already-targeted allele. Presuming a 50% chance for each allele to be targeted, the probability for this event to occur randomly is very low ($p=0.3\times10^{-8}$). Similar results were obtained when attempting to sequentially disrupt both alleles of FANCD2 in a second human adenocarcinoma line (PL5). Targeting of the second allele in FANCD2$^{+/-}$ PL5 clones yielded 20 clones that had reintegrated the targeting construct into the already-targeted allele ($p=0.1\times10^{-6}$) (FIG. 3B). In contrast, gene targeting of FANCG and FANCC in RKO yielded various nullizygous clones, and the respective alleles were targeted approximately at the expected rates.

Example 14

Gene Targeting of BRCA2

One allele of the BRCA2 gene was disrupted in RKO cells by replacing the distal part of exon 11, causing a premature stop codon after BRC repeat 5. Thirteen viable clones having homologous integration of the targeting construct were obtained during several independent targeting rounds, all of which had integrated the targeting construct into the already-mutant allele (5355AA) ($p=0.0001$) (FIG. 3C). Five clones with presence of both, wild type and mutant alleles were identified as being tetraploid.

Example 15

Exclusion of Common Artifacts During Gene Targeting

Steps were taken to exclude common artifacts that could occur during gene targeting. To exclude that the recombinant FANCD2$^{+/-}$ clones were contaminated with nonrecombinant cells, a PCR assay was performed and cells were reselected with hygromycin. Neither PCR products of the hygromycin gene nor hygromycin-resistant colonies were found. Using allele-specific PCR and direct sequencing, no significant nucleotide differences of the homologous regions between the FANCD2 targeting construct and the nontargeted FANCD2 allele were detected, which could have caused the preferential integration of the construct into one particular allele. The presence of a third FANCD2 allele was excluded by whole-chromosome 3 painting and FISH analysis using a FANCD2-specific probe. In RKO cells, a small piece of chromosome 3 (in addition to two normal chromosome 3 copies) was found attached to another chromosome. However, the signal from the FANCD2-specific probe was observed only on the two normal chromosomes. In PL5, two chromosomes painted completely and probe signal was observed on both copies (FIG. 3D).

Example 16

Cell Proliferation and Cell Cycle Profile Upon Partial Depletion of FANCD2

Figure 4:
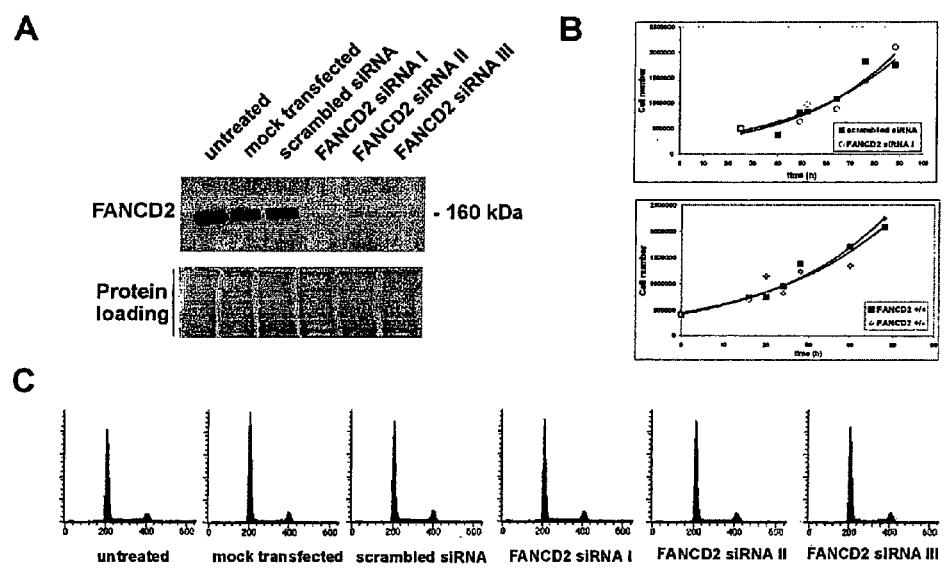
FIG. 4. No obvious selective disadvantage upon partial depletion of FANCD2. (A) FANCD2 immunoblotting to assess the efficiency of siRNA-mediated depletion of FANCD2 protein 48 h after transfection. (B) Cell proliferation of FANCD2-depleted (upper graph) or $FANCD2^{+/-}$ cells (lower graph) as compared to control cells transfected with scrambled siRNA or left untreated, respectively. (C) Cell cycle analysis of FANCD2-depleted cells 72 h after transfection.
Figure 5:
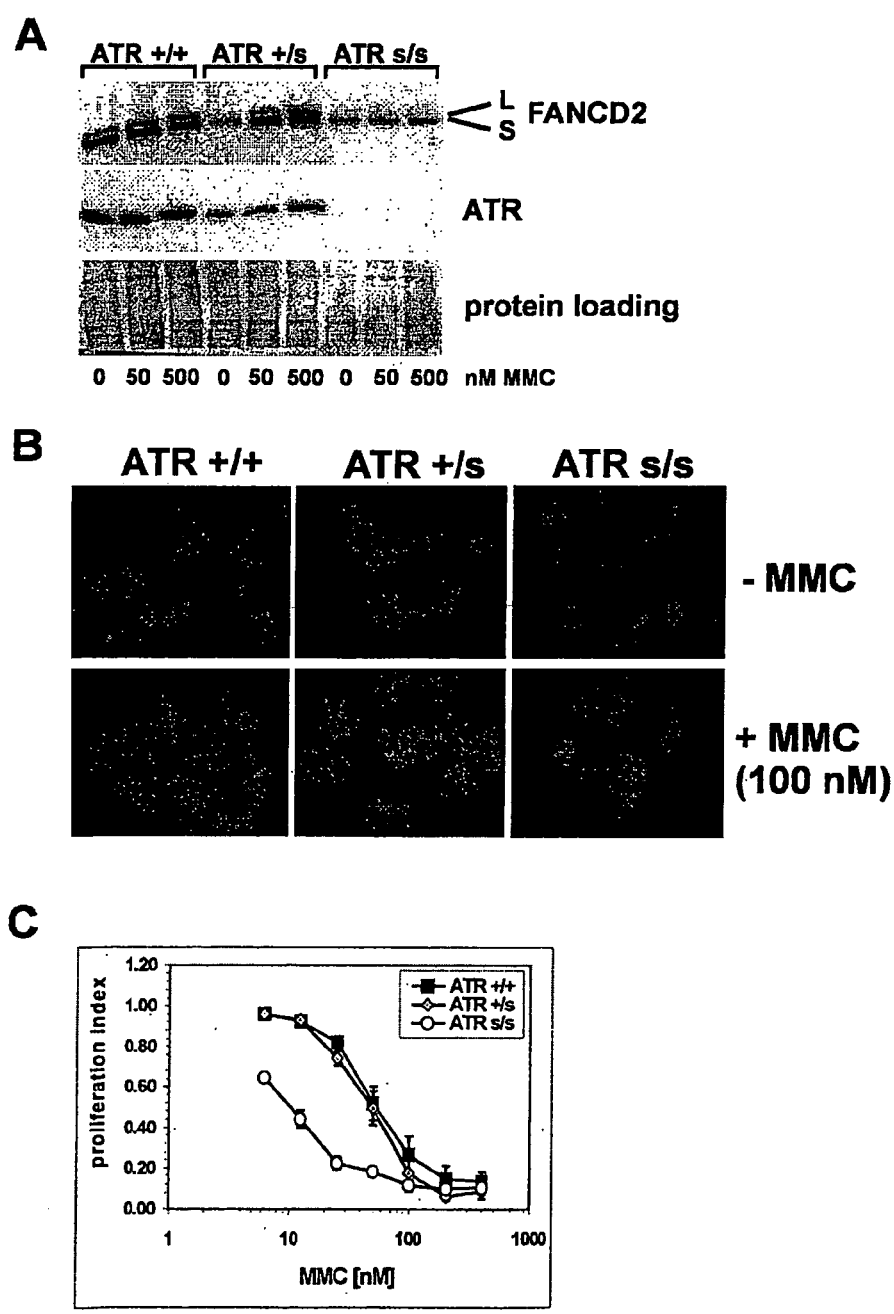
FIG. 5 ATR-dependent FANCD2/FA pathway functions. Parental DLD1 colorectal cancer cells ($ATR^{+/+}$), were compared to DLD1 cells having a heterozygote ($ATR^{+/s}$) or homozygote ($ATR^{s/s}$) knock-in mutation (2101A→G) in the following assays. (A) FANCD2 and ATR immunoblotting to assess ATR-dependent FANCD2 monoubiquitination (S=nonmonoubiquitinated FANCD2, L=monoubiquitinated FANCD2) 24 h after treatment with incremental MMC concentrations) (B) ATR-dependent FANCD2 nuclear focus formation 24 h after MMC at 100 nM. (C) Proliferation assays to assess MMC sensitivity of $ATR^{+/+}$, $ATR^{+/s}$ and $ATR^{s/s}$ DLD1 cells 6 d after treatment. Error bars represent SEM of four independent experiments.

Cell death, proliferation, and cell cycle profiles were assessed in FANCD2 protein-depleted cells, using FANCD2 siRNA. The depletion efficiency was confirmed by immunoblotting 48 h after transfection (FIG. 4A). The fraction of dead cells in the FANCD2-depleted cells as compared to untreated, mock-transfected and scrambled-siRNA transfected control cells was not increased, when examined one to four days after transfection. Also, no gross differences were observed in growth kinetics between FANCD2-depleted and control cells (FIG. 4B, upper graph). Cell cycle analysis did not reveal abnormalities in the FANCD2-depleted cells 72 h after siRNA transfection (i.e. 24 h after demonstrable FANCD2 protein depletion) (FIG. 4C). Similarly, no significant differences in cell death, cell growth and cell cycle profiles were detected between parental and FANCD2$^{+/-}$ cells (FIG. 4B, lower graph and data not shown).

Example 17

ATR-Dependent FANCD2 Modifications and MMC Sensitivity

Using the recently engineered DLD1 colorectal adenocarcinoma cells harboring a knock-in mutation of the ATR gene (2101A→G) that is predicted to drastically decrease ATR protein levels, a p53-mutant cancer cell model a previous report on ATR-dependent FANCD2 modifications was extended. DLD 1 cells having subtotal depletion of ATR protein (ATR$^{th}$) were defective in the upregulation of FANCD2 monoubiquitination (FIG. 4A) and in FANCD2 nuclear focus formation (FIG. 4B) upon DNA-damage induced by treatment with the DNA interstrand-crosslinking agent MMC. Furthermore, ATR$^{th}$ cells were strikingly more sensitive to MMC than control cells (FIG. 4C). This MMC hypersensitivity was quantitatively comparable to that of FANCC$^{14-}$ and FANCG$^{-1"}$ cancer cells.

Example 18

Construction of the Hemizygous BRCA2 Variant Library

The phase-determined BRCA2-hemizygous cells are used for sequential targeting of the remaining functional BRCA2 allele using a complex and partially degenerate library of targeting constructs. First, a series of promoterless AAV vectors are constructed, each of whose flanking homologous arms included a single intact exon of BRCA2, creating a distinct vector for each exon. Second, through site directed mutagenesis, individual silent mutations, those not affecting the amino acid translation, are introduced into the exon sequences of each exon to serve as positive controls for the library and, as appropriate, individual potentially deleterious mutations are introduced that are of medical interest to enrich and ensure their representation at adequate numbers within the library. Third, partially degenerate exons are created using mutation-prone PCR on the arm containing the exon, at a density (tested by sequencing of individual clones from the PCR product) and that is dominated by plasmids containing three to ten amino acid-altering mutations per plasmid. Fourth, for each exon, the AAV constructs are mixed to form a pool containing single-mutant and multiple-mutant exons. Fifth, the AAV constructs are introduced into the phased cells, selected for integration at the correct genomic location, and expand each resultant cell clone. The collection of individual clones resulting from targeting each exon represents an uncharacterized BRCA2 variant library.

To create the hemizygous BRCA2 variant library, it is necessary to determine, for each clone of the uncharacterized library, whether the final targeting event has affected the functional or the nonfunctional allele. To do this, the phase of the new integrant sequence with respect to the intronic markers of the phased cell is determined for each clone. PCR primers, one matching the targeting construct and one flanking the other side of the intronic tag, identifies which of the two alleles has been targeted in the second targeting round. The clones having integrated the final construct into the pre-existing non-functional allele are tabulated and constitute the reference rate of integration, for further deleterious effects could not be expected in such clones. These also constitute the reference variant library. Contrasting to this library, the clones having integrated the final construct into the pre-existing functional allele are tabulated and constitute the hemizygous BRCA2 variant library. In this latter library, the mutant constructs are allelic to an irrelevant nonfunctional allele and they can functionally and for convenience considered as hemizygous for the new variants.

Example 19

Constructing the Database

The reference library is sequenced selectively to form a reference database. For each exon targeted, the same exon within each derived clone is sequenced. The variance among the exonic mutations, and the frequency of wildtype exons, reflected the variation in sequences of the effective AAV construct pool utilized in the final targeting step. The ratio of silent single-site mutations to wild-type exons is expected to be very high, confirming that nearly all clones represent integration of the exogenous exon, which is provided in the homology arm of the vector.

The targeted exons of the hemizygous BRCA2 variant library similarly are sequenced to construct a hemizygous variant database. Unlike the reference database, the hemizygous database reflects both the final AAV construct pool and the effect of deleterious function of the included deleterious mutations, which serve to eliminate some clones from the library. The ratio of exons having silent site mutations to those having wild-type exons is compared to that of the reference library; the comparison is expected to confirm a similar exon-replacement efficiency for the reference and the hemizygous libraries. Mutations creating the same amino acid change were grouped in the analysis of the results. The mutations found frequently in the hemizygous variant library define a database of benign mutations of BRCA2. Some mutations are found at a frequency that is reduced as compared to the reference library, and these mutations constituted a database of hypomorphic variants, and the degree of under-representation constitute a measure of deleterious effect for each mutation. For variants of BRCA2 within exon 27, our results from a syngeneic variance library, studied by such sequencing and database construction, were published (Hucl et al, Cancer Research, 2008, incorporated herein by reference).

Table 2. Information regarding start sites, intro/exon junctions, transcriptional termination sites and other information relevant to the sequence can be found at the Accession number each of which is incorporated herein by reference in the version of the sequence available as of the priority date of the application.

TABLE 2

Information regarding start sites, intro/exon junctions, transcriptional termination sites and other information relevant to the sequence can be found at the Accession number each of which is incorporated herein by reference in the version of the sequence available as of the priority date of the application.

| Name | Abbreviation | Accession No | Region | SEQ ID NO |
|---|---|---|---|---|
| breast cancer 1 | BRCA1 | NG_005905 | 10511 . . . 91665 | 1 |
| breast cancer 2 | BRCA2 | NM_000059 | | 2 |
| mutL homolog 1 | MLH1 | NG_007109 | 5001 . . . 62359 | 3 |
| mutS homolog 2 | MSH2 | NG_007110 | 5001 . . . 85098 | 4 |
| mutS homolog 6 | MSH6 | NG_007111 | 4936 . . . 28807 | 5 |
| ephrin receptor EphA3 | EPHA3 | NC_000003 | 89239364 . . . 89613974 | 6 |
| ephrin receptor EphA4 | EPHA4 | NC_000002 | 221990991 . . . 222145254 | 7 |
| ephrin receptor EphB2 | EPHB2 | NC_000001 | 22909918 . . . 23114410 | 8 |
| integrase interactor 1 | INI1 | NC_000022 | 22459150 . . . 22506705 | 9 |
| axin 1 | AXIN1 | NC_000016 | 277441 . . . 342465 | 10 |
| axin2 | AXIN2 | NC_000017 | 60955143 . . . 60988227 | 11 |
| myeloid/lymphoid or mixed-lineage leukemia 3 | MLL3 | AC_000068 | 151159181 . . . 151460261 | 12 |
| E1A binding protein p300 | EP300 | NC_000022 | 39818553 . . . 39906024 | 13 |
| neurofibromin 1 | NF1 | NC_000017 | 26446121 . . . 26728821 | 14 |
| TP53 tumor protein p53 | TP53 | NC_000017 | 7512445 . . . 7531642 | 15 |
| adenomatous polyposis coli | APC | NC_000005 | 112101483 . . . 112209835 | 16 |
| von Hippel-Lindau tumor suppressor | VHL | NC_000003 | 10158319 . . . 10168762 | 17 |
| SMAD family member 2 | SMAD2 | NC_000018 | 43613464 . . . 43711510 | 18 |
| SMAD family member 4 | SMAD4 | NC_000018 | 46810611 . . . 46860145 | 19 |

TABLE 2-continued

Information regarding start sites, intro/exon junctions, transcriptional termination sites and other information relevant to the sequence can be found at the Accession number each of which is incorporated herein by reference in the version of the sequence available as of the priority date of the application.

| Name | Abbreviation | Accession No | Region | SEQ ID NO |
|---|---|---|---|---|
| kelch-like ECH-associated protein 1 | KEAP1 | AC_000062 | 10491509 ... 10508764 | 20 |
| cyclin-dependent kinase inhibitor 2A | CDKN2A | NC_000009 | 21957751 ... 21984490 | 21 |
| retinoblastoma 1 | RB1 | NC_000013 | 47775884 ... 47954027 | 22 |
| elongation factor RNA polymerase II | MEN | NC_000019 | 18414473 ... 18493918 | 23 |
| neurofibromin 2 | NF2 | NC_000022 | 28329565 ... 28424587 | 24 |
| patched homolog 1 | PTCH | NG_007664 | 5001 ... 78984 | 25 |
| transforming growth factor, beta receptor 1 | TGFBR1 | NC_000009 | 100907233 ... 100956295 | 26 |
| transforming growth factor, beta receptor II | TGFBR2 | NG_007490 | 5001 ... 92641 | 27 |
| activin A receptor, type IB | ACVR1B | NC_000012 | 50631753 ... 50677127 | 28 |
| activin A receptor, type IIA | ACVR2A | NC_000002 | 148319040 ... 148404863 | 29 |
| meiotic recombination 11 homolog A | MRE11 | NC_000011 | 93790114 ... 93866688 | 30 |
| mitogen-activated protein kinase kinase 4 | MAP2K4 | NC_000017 | 11864860 ... 11987776 | 31 |
| serine/threonine kinase 11 | LKB1/STK11 | NG_007460 | 5001 ... 27637 | 32 |
| ataxia telangiectasia mutated | ATM | NC_000011 | 107598769 ... 107745036 | 33 |
| ataxia telangiectasia and Rad3 related | ATR | NC_000003 | 143650767 ... 143780358 | 34 |
| Fanconi anemia, complementation group D2 | FANCD2 | NG_007311 | 5001 ... 80502 | 35 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09309511B2). An electronic copy of the "Sequence Listing" will also be available from the USPTO upon request and payment of the fee set forth in 37 CFR 1.19(b)(3).

What is claimed is:

1. A method for classifying relative deleteriousness of a mutation in a nucleic acid sequence of a gene to a mammalian cell comprising:
   providing an isolated mammalian cell comprising a genome comprising a single functional copy of a first gene and a non-functional copy of the first gene;
   transforming the cell with a nucleic acid construct comprising a nucleic acid sequence from a second gene comprising the mutation to be classified, wherein the nucleic acid sequence from the second gene comprises a mutated first gene or a mutated fragment of the first gene, wherein the nucleic acid sequence from the second gene is flanked by two nucleic acid sequences to allow recombination with the genome of the cell in the first gene;
   detecting a frequency of recombination of the nucleic acid sequence from the second gene in the functional copy of the first gene,
   detecting a frequency of recombination of the nucleic acid sequence from the second gene in the non-functional copy of the first gene,
   comparing the frequency of recombination in the functional copy of the first gene to the frequency of recombination in the non-functional copy of the first gene, wherein an equal or higher frequency of recombination of the nucleic acid sequence from the second gene in the functional copy of the first gene compared to the non-functional copy of the first gene is indicative of a non-deleterious mutation to a mammalian cell, and wherein a lower frequency of recombination of the nucleic acid sequence from the second gene in the functional copy of the first gene compared to the non-functional copy of the first gene is indicative of a deleterious mutation to a mammalian cell.

2. The method of claim 1, wherein the nucleic acid sequence from the second gene comprising a mutation comprises a fragment of the first gene that is present as a single functional copy in the cell.

3. The method of claim 1, wherein the first gene, or the second gene, or both the first and second genes are suspected of being tumor-suppressor genes.

4. The method of claim 1, wherein the cell comprises a library of cells comprising members comprising different single functional first genes.

5. The method of claim 1, further comprising providing a library of nucleic acid constructs comprising a nucleic acid sequence from a second gene.

6. The method of claim 1, wherein the mutation in the second gene is in a gene region selected from an intron, an exon, a 3'-UTR, 5'-UTR, transcriptional regulatory region, translational regulatory region, and a region at a junction between two of the regions.

7. The method of claim 1, wherein at least one of the flanking sequences is not present in a non-functional copy of the first gene in the mammalian cell.

8. The method of claim 1, further comprising performing a functional assay on a cell after detecting recombination.

9. The method of claim 1, wherein the mammalian cell is a somatic cell.

* * * * *